United States Patent [19]
Lorenzen et al.

[11] Patent Number: 4,865,054
[45] Date of Patent: Sep. 12, 1989

[54] METHOD OF AND APPARATUS FOR MAKING AND PROCESSING STREAMS OF FIBROUS MATERIAL OF THE TOBACCO PROCESSING INDUSTRY

[75] Inventors: Heinz-Christen Lorenzen, Wentworf; Uwe Heitmann; Wolfgang Siems, both of Hamburg, all of Fed. Rep. of Germany

[73] Assignee: Körber AG, Hamburg, Fed. Rep. of Germany

[21] Appl. No.: 150,526

[22] Filed: Jan. 29, 1988

[30] Foreign Application Priority Data

Jan. 31, 1987 [DE] Fed. Rep. of Germany ....... 3702961

[51] Int. Cl.$^4$ .............................................. A24C 5/14
[52] U.S. Cl. ................................... 131/280; 131/84.1; 131/84.4; 131/905; 131/906; 131/908
[58] Field of Search ................... 131/84.1, 905, 906, 131/908, 84.4, 280

[56] References Cited

U.S. PATENT DOCUMENTS

| 3,056,026 | 9/1962 | Bigelow . | |
|---|---|---|---|
| 3,557,374 | 1/1971 | Schmermund | 131/908 X |
| 3,738,376 | 6/1973 | Labbe et al. | 131/906 X |
| 4,024,394 | 5/1977 | Reuland . | |
| 4,025,770 | 5/1977 | Reuland . | |
| 4,063,563 | 12/1977 | Lorenzen | 131/84.4 |
| 4,147,173 | 4/1979 | Reuland . | |
| 4,185,644 | 1/1980 | Heitmann et al. . | |
| 4,190,061 | 2/1980 | Heitmann et al. . | |
| 4,196,740 | 4/1980 | Rudszinat | 131/84.4 X |
| 4,236,534 | 12/1980 | Heitmann et al. . | |
| 4,280,516 | 7/1981 | Reuland | 131/84.1 X |
| 4,284,087 | 8/1981 | Reuland | 131/84.1 X |
| 4,290,436 | 9/1981 | Reuland | 131/84.1 X |
| 4,350,170 | 9/1982 | Baier . | |
| 4,423,742 | 1/1984 | Reuland . | |
| 4,424,443 | 1/1984 | Reuland . | |
| 4,474,190 | 10/1984 | Brand | 131/84.1 |
| 4,556,071 | 12/1985 | Hoffmann | 131/84.4 |
| 4,595,027 | 6/1986 | Higgins et al. | 131/280 |
| 4,616,139 | 10/1986 | Heitmann . | |
| 4,638,817 | 1/1987 | Okumoto | 131/84.1 X |
| 4,645,921 | 2/1987 | Heitmann et al. . | |
| 4,653,516 | 3/1987 | Mattei | 131/906 |

FOREIGN PATENT DOCUMENTS

| 759532 | 10/1956 | United Kingdom . | |
|---|---|---|---|
| 2128466 | 5/1984 | United Kingdom | 131/84.4 |
| 2133965 | 8/1984 | United Kingdom | 131/84.4 |

Primary Examiner—V. Millin
Assistant Examiner—Joe H. Cheng
Attorney, Agent, or Firm—Peter K Kontler

[57] ABSTRACT

One or more streams of tobacco in a rod making machine are tested by several density monitoring units one of which employs a source of nuclear radiation and at least one other of which employs a source of optical radiation. The resulting density signals are evaluated and converted into signals which are devoid of the influence of changes of color and/or blend of fibrous material in the stream or streams and are used for segregation of defective rod-shaped articles and/or for controlled removal of surplus from the stream or streams.

38 Claims, 5 Drawing Sheets

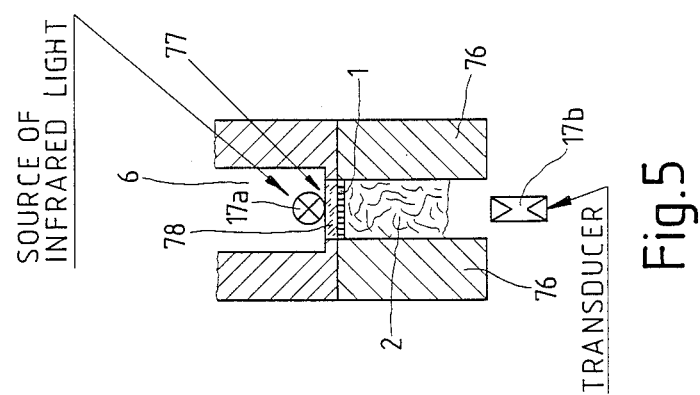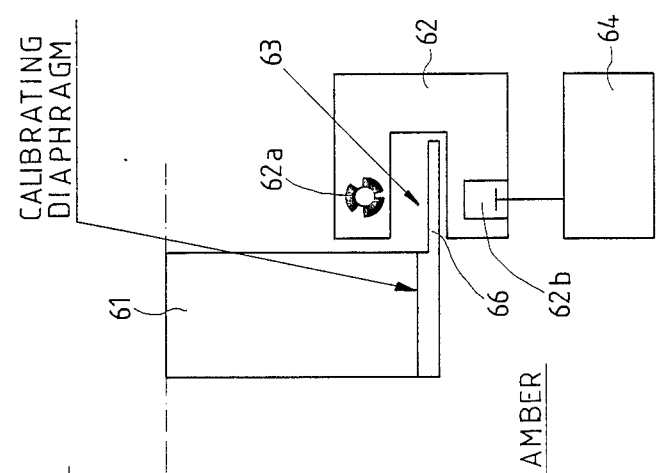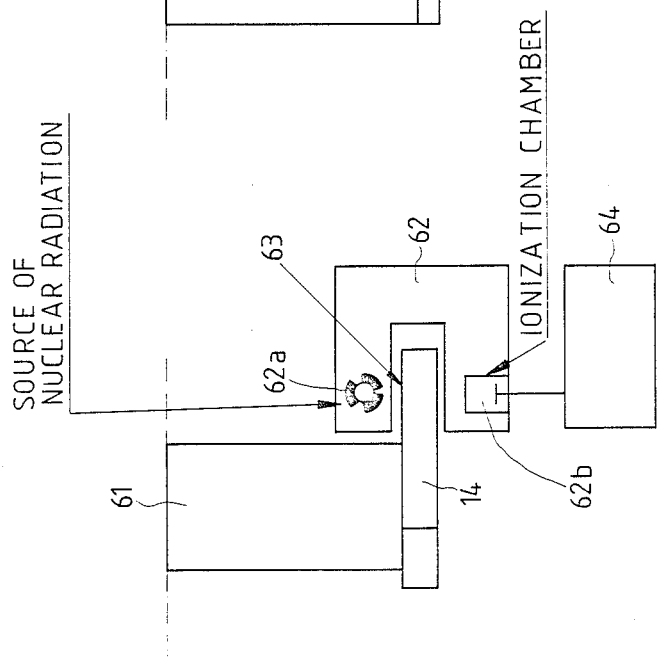

METHOD OF AND APPARATUS FOR MAKING AND PROCESSING STREAMS OF FIBROUS MATERIAL OF THE TOBACCO PROCESSING INDUSTRY

CROSS-REFERENCE TO RELATED CASES

Commonly owned copending patent application Ser. No. 572,563 filed Jan. 18, 1984 by Henning Moller et al. discloses a method of and an apparatus for monitoring and evaluating the density of a tobacco stream with X-rays at a plurality of different distances from a reference plane.

Another density monitoring device is disclosed in commonly owned copending patent application Ser. No. 930,251 filed Nov. 12, 1986 by Werner Hartmann et al.

The assignee of the present application is the owner of numerous additional pending United States and foreign patent applications, as well as of numerous United States and foreign patents and printed publications, all of which disclose density measurement of streams of tobacco and/or other fibrous materials of the tobacco processing industry by resorting to nuclear and/or optical density monitoring units.

BACKGROUND OF THE INVENTION

The present invention relates to improvements in methods of and apparatus for forming and/or processing one or more streams of fibrous material of the tobacco processing industry, especially to improvements in a method of and in an apparatus for ascertaining the density of one or more wrapped or unwrapped streams of natural, substitute and/or reconstituted tobacco and for utilizing the results of density measurement or measurements to improve the quality of smokers' products, such as filter rod sections and plain or filter tipped cigarettes, cigars, cigarillos or cheroots.

A machine which is used for mass production of cigarettes or other rod-shaped articles of the tobacco processing industry is expected to turn out long series of rod-shaped articles which exhibit identical or practically identical properties as concerns their appearance, taste, weight, feel and resistance to the flow of tobacco smoke therethrough. This ensures that the purchaser of such articles is not annoyed by pronounced deviations of actual characteristics from desirable and accustomed characteristics of her or his brand of smokers' products. For example, a smoker expects that each and every article in a pack of plain or filter cigarettes will exhibit the same resistance to deformation by finger pressure, that each and every article will offer the same resistance to the flow of smoke from the lighted end toward and through the filter mouthpiece or directly into the mouth, and/or that the customary perforations in the wrapper of each article will admit identical quantities of cool atmospheric air. In order to ensure that all articles of a long series of articles which are turned out by cigarette making, filter tipping and like machines will exhibit identical desirable properties, it is necessary to continuously monitor at least some variable characteristics of the constituents of smokers' products and to continuously influence the manufacturing operation so as to eliminate the unwanted influence of variable characteristics upon the desirable parameters of the products. One of the variable parameters is the density of the stream of fibrous material which is draped into a web of cigarette paper, tipping paper or other suitable wrapping material in order to form a rod which can be subdivided into discrete plain cigarettes, cigars, cigarillos or cheroots of unit length or multiple unit length, into discrete filter rod sections of desired length or into discrete filter cigarettes, cigars, cigarillos or cheroots of unit length or multiple unit length.

OBJECTS AND SUMMARY OF THE INVENTION

An object of the invention is to provide a novel and improved method of ascertaining the density and utilizing the ascertained density of one or more streams of fibrous material of the tobacco processing industry, such as one or more streams which consist of or contain natural, substitute or reconstituted tobacco or filter material for tobacco smoke.

Another object of the invention is to provide a method which renders it possible to ascertain the density of one or more moving streams of fibrous material in a novel and improved way and to utilize in a novel way the results of density measurements so as to counteract fluctuations of density as well as fluctuations of other variable characteristics of the stream or streams in order to ensure the making of smokers' products which are superior to heretofore known products.

A further object of the invention is to provide a method which renders it possible to counteract the adverse effects of changes of tobacco blends in tobacco streams without the need for direct and/or exclusive monitoring of such changes.

An additional object of the invention is to provide a method which renders it possible to counteract the undesirable effects of changes of color of tobacco in a tobacco stream without the need for direct or exclusive monitoring of such changes.

Still another object of the invention is to provide a method which renders it possible to simultaneously influence the making of rod-shaped articles from two or more simultaneously produced streams of tobacco or other fibrous material of the tobacco processing industry.

Another object of the invention is to provide a novel and improved means for monitoring the density of two or more simultaneously produced streams of tobacco or other fibrous material of the tobacco processing industry.

A further object of the invention is to provide a method which renders it possible to influence the removal of surplus from one or more tobacco streams in a number of different ways so as to enhance the making of cigarettes or other rod-shaped smokers' products exhibiting optimum parameters which are important to smokers, such as appearance, feel, resistance to the flow of tobacco smoke and others.

An additional object of the invention is to provide a method which renders it possible to regulate the rate of removal of surplus of fibrous material from a single tobacco stream or from two or more simultaneously produced tobacco streams with a heretofore unmatched degree of reliability and accuracy.

Another object of the invention is to provide a method of monitoring variable characteristics of one or more streams of fibrous material of the tobacco processing industry in such a way that the monitoring operation, or at least one important step of the monitoring operation, takes place in immediate or close proximity of the locus where the products leave the machine or the production line so as to avoid the possibility of undesirable changes of parameters of such products downstream of the location of the last monitoring step.

A further object of the invention is to provide a method which renders it possible to simultaneously monitor and counteract changes of two or more variable characteristics of one or more moving streams of fibrous material of the tobacco processing industry.

Still another object of the invention is to provide a method of making plain cigarettes and of segregating defective cigarettes from satisfactory cigarettes whenever the ascertained density of the filler in a cigarette is outside of an accurately determined range of acceptable densities, and to practice such method in or with a machine which is designed to turn out many thousands of cigarettes per minute.

An additional object of the invention is to provide a novel and improved apparatus for the practice of the above outlined method and to provide the apparatus with novel and improved means for simultaneously ascertaining deviations of two or more different variable characteristics of one or more streams from optimum characteristics.

Another object of the invention is to provide the apparatus with novel and improved density measuring or monitoring means.

A further object of the invention is to provide the apparatus with novel and improved means for processing signals which denote densities of several simultaneously produced streams of fibrous material or the density of a single stream of fibrous material during different stages of conversion of the stream or streams into a succession of rod-shaped articles of the tobacco processing industry.

Another object of the invention is to provide the apparatus with novel and improved means for conveying one or more streams of fibrous material of the tobacco processing industry.

An additional object of the invention is to provide the apparatus with novel and improved means for utilizing the results of density measurements to prevent deviations of one, two or more important parameters of ultimate products from optimum parameters.

A further object of the invention is to provide an apparatus which can be installed in existing machines or production lines as a superior substitute for existing apparatus.

Another object of the invention is to provide an apparatus wherein certain variable characteristics of one or more streams of fibrous material need not be monitored by specially designed equipment but the undesirable influence of changes of such characteristics upon the ultimate products can be eliminated or counteracted in a simple and inexpensive way.

Another object of the invention is to provide a machine or a production line which embodies the above outlined apparatus and wherein rod-shaped articles of the tobacco processing industry are turned out and processed in accordance with the above outlined method.

Still another object of the invention is to provide the apparatus with novel and improved means for initiating segregation of defective or even potentially defective rod-shaped articles of the tobacco processing industry from satisfactory rod-shaped articles.

A further object of the invention is to provide novel and improved optical density monitoring means for use in the above outlined apparatus.

An additional object of the invention is to provide novel and improved apparatus for simultaneously forming and processing several streams of fibrous material of the tobacco processing industry.

Another object of the invention is to provide the apparatus with novel and improved means for removing surplus of fibrous material from one or more moving streams of tobacco or the like.

A further object of the invention is to provide the apparatus with novel and improved means for monitoring the quality of rod-shaped articles in a cigarette making or like machine.

An additional object of the invention is to provide the apparatus with novel and improved means for evaluating two or more simultaneously generated signals which denote the density of a single tobacco stream or the densities of several simultaneously produced streams.

A further object of the invention is to provide an apparatus wherein the parameters of rod-shaped articles of the tobacco processing industry can be influenced in a novel and improved way with a view to turn out articles which are not affected by changes of density, color and/or blend of fibrous material in the stream or streams from which the articles are made.

An additional object of the invention is to provide a novel and improved device for monitoring the density and other variable characteristics of a single stream or of two or more streams of fibrous material of the tobacco processing industry during different stages of conversion of the stream or streams into the filler or fillers of one or more rods which are ready to be subdivided into rod-shaped smokers' articles.

Another object of the invention is to provide an apparatus which can detect soft spots in the fillers of cigars, cigarillos cheroots or filter rod sections.

A further object of the invention is to provide an apparatus which can reliably segregate rod-shaped articles with soft spots from acceptable rod-shaped articles of the tobacco processing industry.

One feature of the present invention resides in the provision of a method of ascertaining the density of at least one stream of fibrous material of the tobacco processing industry, especially a wrapped or unwrapped tobacco stream. The method comprises the steps of directing against the stream at least one beam of radiation which is capable of penetrating through (particularly across) the stream whereby the intensity of radiation which has penetrated through the stream at least indirectly denotes the density of the stream, and generating at least one density signal which is indicative of the intensity. The method can be practiced with particular advantage to ascertain the density of a stream which, in addition to density, exhibits at least one further variable characteristics, such as the color and/or composition of its constituents (for example, the color of burley is or can be different from that of oriental tobacco, and the composition of the constituents of a tobacco stream can change in that a first length contains a first mixture or blend and a next-following second length of the stream contains a different second mixture or blend of natural, substitute or reconstituted tobacco). The directing step of such method can comprise pointing or aiming against or at the stream (e.g., at right angles to the direction of advancement of a continuously moving stream) at least one beam of a first radiation which is influenced by the further characteristic of the stream in a first manner, and pointing or aiming against or at the stream at least one beam of a second radiation which is influenced by the further characteristic of the stream in a different second manner (for example, one of the beams is not, influenced by the further characteristic in any manner and the other beam is absorbed or intercepted by the stream which exhibits the further characteristics to a much greater extent than the one beam). The generating step of such method includes generating at least one first density signal indicative of the intensity of that portion of the first radiation which has penetrated through the stream, and generating at least one second density signal indicative of the intensity of that portion of the second radiation which has penetrated through the stream. The just outlined method can further comprise the step of modifying one of the first and second density signals by the other of the first and second density signals so as to at least substantially eliminate the influence of the further characteristic upon the modified one signal.

The first radiation can include or constitute nuclear radiation (such as beta rays) or X-rays, and the second radiation can include or constitute optical radiation (such as infrared rays).

The method preferably further comprises the steps of forming the stream with a surplus of fibrous material, conveying the stream longitudinally in a predetermined direction along a predetermined path (e.g., along a substantially horizontal path), modifying one of the first and second signals by the other of the first and second signals for the aforementioned purpose of at least substantially eliminating the influence of the further characteristic(s) upon the modified one signal, removing the surplus from the stream in a predetermined portion of the path at a rate which is a function of the modified one signal, and draping the stream into a web of wrapping material (e.g., into a web or strip of cigarette paper or into a web or strip of so-called tipping paper which is used in filter tipping machines for the making of filter cigarettes) in a second portion of the path downstream of the predetermined portion. The first radiation is preferably a nuclear radiation, and the second radiation is preferably an optical radiation, i.e., the modified signal is preferably a signal which is generated to denote the intensity of optical radiation that has penetrated through the stream.

The just described method which includes removing the surplus from the stream can be carried out in such a manner that the directing step includes pointing against the stream at least one first beam of optical radiation in a path portion upstream of the predetermined portion of the path, and pointing against the stream at least one second beam of optical radiation in a path portion downstream of the predetermined portion. The generating step then includes generating at least one first density signal to denote the intensity of optical radiation which has penetrated across the stream upstream of the predetermined portion and generating at least one second density signal denoting the intensity of optical radiation which has penetrated across the stream downstream of the predetermined portion of the path. The first and second density signals of such method are processed to form an additional signal which denotes the quantity of removed surplus of fibrous material. The directing step of this method can further comprise pointing at least one beam of nuclear radiation at the stream in the path, and the generating step then further includes generating at least one signal which is indicative of the intensity of nuclear radiation that has penetrated across the path, and this method then further comprises the step of correcting at least one of the first and second density signals (which denote the intensities of beams of optical radiation that has penetrated through the stream upstream and downstream of the locus of removal of the surplus) when the at least one of the first and second density signals deviates from the density signal which has been generated to denote the intensity of nuclear radiation that has penetrated through the stream.

The method can comprise the steps of forming at least two preferably parallel streams of fibrous material and conveying the two parallel streams along discrete predetermined paths. The directing step of such method can comprise pointing or aiming against the stream in at least one of the paths at least one beam of nuclear radiation which is influenced by the further characteristic(s) of the at least one stream in a first manner, and pointing or aiming at each of the streams at least one beam of optical radiation which is influenced by the further characteristic(s) of the respective streams in a different second manner. The generating step of such method can include generating a first density signal indicative of the intensity of nuclear radiation which has penetrated through the stream in the at least one path, generating a first second density signal indicative of the intensity of optical radiation which has penetrated through one of the streams, and generating a second second density signal indicative of optical radiation that has penetrated across another stream. Such method further comprises the step of modifying each of the second signals by the first signal so as to at least substantially eliminate the influence of the further characteristic(s) from the second signals. Such method can also comprise the step of draping the streams into discrete strips or webs of wrapping material.

The just discussed method can be modified as follows: At least one of the streams can be subdivided into a file of successive rod-shaped articles (e.g., plain cigarettes of unit length or multiple unit length) upon completion of the draping step, and the directing step can include pointing or aiming at least one beam of nuclear radiation at successive rod-shaped articles of the file. At least one of the second signals is then modified by the signals which are generated to denote the intensity of nuclear radiation which has passed through successive rod-shaped articles of the file. The rod-shaped articles are preferably transported sideways, i.e., at right angles to their respective longitudinal axes, in the form of one or more rows of parallel articles. Such mode of transporting rod-shaped articles is desirable or necessary in many types of modern machines for the processing of rod-shaped articles of the tobacco processing industry, e.g., in filter tipping machines wherein plain cigarettes of unit length or multiple unit length are connected with filter mouthpieces of unit length or multiple unit length to form filter cigarettes of unit length or multiple unit length. As a rule, the first signals will be used to correct at least that second signal which is generated to denote the density of the stream which is thereupon subdivided into rod-shaped articles. The subdividing step preferably includes severing the corresponding wrapped stream in a preselected portion of the respective path by a so-called cutoff.

As mentioned above, the additional or further variable characteristic(s) of a stream can include the color of its fibrous material and/or the composition (blend) of its constituents.

If a stream contains a surplus of fibrous material which is removed in a predetermined portion of the path prior to draping of the stream into a web or strip of cigarette paper or other suitable wrapping material, the removal of surplus can be regulated as a function of first signals which are generated to denote the intensity of nuclear radiation that has penetrated through the stream, and such regulating step can be influenced by further signals which denote the intensity of optical radiation that has penetrated through the stream; however, such further signals are preferably modified (corrected) as a function of the first signals prior to their application as a means for regulating the removal of surplus in superimposition upon the regulation by the first signals.

Optical signals which are generated to denote the intensity of an optical radiation that has penetrated through successive increments of a moving stream of fibrous material can be compared with a reference signal denoting a predetermined range of acceptable densities, and the signals which are outside of such range can be utilized to segregate the respective (unsatisfactory) rod-shaped articles from the remaining (acceptable) rod-shaped articles which are obtained upon draping of the trimmed stream and as a result of subdivision of the draped stream into discrete rod-shaped articles. The surplus removing step of such method can be regulated by signals which are obtained by determining the intensity of at least one beam of nuclear or optical radiation that has penetrated across the stream prior or subsequent to draping and is indicative of the density of successive increments of the stream.

Another feature of the invention resides in the provision of an apparatus for processing at least one stream of fibrous material of the tobacco processing industry, especially a wrapped or unwrapped stream of artificial, natural and/or reconstituted tobacco. The apparatus comprises density monitoring means including means for directing against or at the at least one stream at least one beam of optical and/or other radiation (such as nuclear radiation or X-rays) which is capable of penetrating through the stream so that the intensity of radiation which has penetrated through the stream at least indirectly denotes the density of the stream, and means for generating at least one density signal indicative of the intensity of radiation which has penetrated through the stream.

As a rule, the at least one stream exhibits two or more variable characteristics, particularly the aforediscussed density and at least one further characteristic such as the color and/or composition of the constituents of the stream. In order to take into consideration one or more further variable characteristics, the directing means of the density monitoring means can comprise means for pointing or aiming at or against the at least one stream at least one beam of a first radiation which is influenced by the at least one further characteristic in a first way (e.g., which is not influenced at all), and means for pointing or aiming at or against the at least one stream at least one beam of a second radiation which is influenced by the at least one further characteristic in a different second way (e.g., much more than the beam of first radiation). The signal generating means of such density monitoring means can comprise a device (e.g., a first transducer) for generating at least one first density signal indicative of the intensity of first radiation which has penetrated through the at least one stream, and a device (such as one or more additional transducer) for generating at least one second density signal indicative of the intensity of second radiation which has penetrated through the at least one stream. Such apparatus can further comprise means for evaluating the first and second density signals, and the evaluating means can comprise means for modifying one of the first and second density signals by the other of the first and second density signals so as to at least substantially eliminate the influence of the at least one further characteristic upon the thus modified one density signal. At least one of the aiming or the pointing means of the density monitoring means can include a source of nuclear radiation, a source of X-rays or a source of optical radiation (such as infrared radiation).

In accordance with a presently preferred embodiment of the density monitoring means, one of the pointing means includes a source of nuclear radiation and the other of the pointing means includes a source of optical radiation. The evaluating means of the apparatus which embodies such density monitoring means preferably comprises means for modifying the signal denoting the intensity of optical radiation which has penetrated through the at least one stream by the signal denoting the intensity of nuclear radiation that has penetrated though the at least one stream. The apparatus which embodies the just outlined density monitoring means can further comprise means for continuously forming the at least one stream with a surplus of fibrous material, means (e.g., an air-permeable endless belt conveyor) for conveying the stream and its surplus in a predetermined direction along a predetermined path, adjustable trimming or equalizing means including means for removing at least some of the surplus from the conveyed stream in a predetermined portion of the path, and means for adjusting the trimming means as a function of the modified signal (i.e., as a function of the signal which has been generated to denote the intensity of optical radiation that has penetrated through the at least one stream and which has been modified by the signal denoting the intensity of nuclear radiation which has penetrated through the at least one stream). Such apparatus can further comprise means for adjusting the trimming means as a function of the signal denoting the intensity of nuclear radiation which has penetrated through the at least one stream so that the adjustment as a function of the modified signal is superimposed upon adjustment as a function of the signal denoting the intensity of nuclear radiation that has penetrated though the at least one stream.

In accordance with a modification, the apparatus comprises means for forming the at least one stream with a surplus of fibrous material, means for conveying the at least one stream and its surplus in a predetermined direction along a predetermined path, and trimming means for removing at least some of the surplus in a predetermined portion of the path. The density monitoring means of such apparatus can comprise a first pointing means having a first source of optical radiation which is aimed at the at least one stream upstream of the predetermined portion of the path and a second pointing means having a second source of optical radiation which is aimed at the at least one stream downstream of the predetermined portion of the path. This apparatus further comprises means for evaluating the signals which denote the intensities of optical radiation from the first and second sources (subsequent to their penetration through the at least one stream) and for generating an additional signal which denotes the quantity of the surplus that is removed from the at least one stream in the predetermined portion of the path. The density monitoring means of the just described apparatus can further comprise means for pointing at the stream at least one beam of nuclear radiation and a device which generates density signals denoting the intensity of nuclear radiation which has penetrated through the at least one stream. The evaluating means then further comprises means for modifying at least one of the signals denoting the intensity of optical radiation by the signal which is indicative of the intensity of nuclear radiation.

The improved apparatus can comprise means for continuously forming at least two discrete streams and means for conveying the streams along separate paths The density monitoring means of such apparatus comprises a source of nuclear radiation which is aimed at one of the streams, and discrete sources of optical radiation (at least one for each of the streams) which are aimed at the respective streams. The signal generating means of such density monitoring means includes a first signal generating device which generates a first density signal denoting the intensity of nuclear radiation which has penetrated through the one stream, and discrete second signal generating devices each arranged to generate a density signal denoting the intensity of optical radiation that has penetrated through the corresponding stream. The apparatus further comprises means for evaluating the signals including means for modifying the second signals denoting the intensities of optical radiation by the first signal which denotes the intensity of nuclear radiation so as to at least substantially eliminate the influence of the at least one further characteristic (if any) upon the second signals, i.e., upon those signals which denote the intensity of optical radiation that has penetrated through the streams. The stream forming means of the just outlined apparatus are preferably designed to form discrete streams each of which contains a surplus of fibrous material, and the apparatus then further comprises adjustable trimming means for each of the streams. Each trimming means includes means for removing the surplus from the respective stream in a predetermined portion of the corresponding path, and the apparatus can further comprise means for adjusting each of the trimming means as a function of the respective modified second signal (denoting the intensity of optical radiation which has penetrated through the respective stream and has been modified by the first signal).

The apparatus which forms at least two discrete streams can further comprise means for draping each stream into a discrete web or strip of suitable wrapping material downstream of the predetermined portion of the respective path (if the apparatus is equipped with means for removing the surplus from the streams), and means (such as one or more conventional cutoff devices) for subdividing each of the draped streams into a series of successive rod-shaped articles. The beam of nuclear radiation can be aimed at successive rod-shaped articles which are obtained from at least one of the draped streams, and the first signals which are obtained as a result of determination of intensity of nuclear radiation which has penetrated through successive rod-shaped articles can be used to modify the second density signals which denote the intensities of optical radiation that has penetrated through the discrete streams so that the thus modified second density signals are devoid or practically devoid of the influence of at least one further variable characteristic of the respective streams. The evaluating means of such apparatus can further include means for modifying the second signal denoting the density of the at least one stream which yields rod-shaped articles that are being tested by nuclear radiation.

In accordance with a further embodiment of the invention, the apparatus can comprise means for conveying the at least one stream along a predetermine path and the directing means of the density monitoring means can comprise at least one source of optical radiation which is aimed at the stream at one side of the path so that the radiation penetrates through the stream and also through the conveying means (either before or after it has penetrated through the stream). The signal generating means of the density monitoring means in such apparatus comprises a device for generating at least one density signal denoting optical radiation which has penetrated through the stream as well as through the conveying means, and such signal generating device is disposed at the other side of the path so that the stream and the conveying means are located between the at least one source of optical radiation and the signal generating device. The latter can comprise an optoelectronic transducer, and the directing means of the density monitoring means can comprise several sources of optical radiation each of which is arranged to point or aim a beam of optical radiation at the stream so that the radiation which has penetrated through the stream impinges upon the transducer.

In accordance with a further embodiment, the apparatus comprises means for forming the at least one stream with a surplus of fibrous material, means for conveying the stream and its surplus along a predetermined path, means for removing at least some of the surplus in a predetermined portion of the path, and means for subdividing the thus trimmed or equalized stream into rod-shaped articles downstream of the predetermined portion of the path. The directing means of the density monitoring means in such apparatus includes means for pointing or aiming at least one beam of optical radiation at the stream in the path, and the signal generating means of such density monitoring means includes a device for generating signals denoting the intensity of optical radiation which has penetrated through successive increments of the stream so that the signals at least indirectly denote the density of successive increments of the stream. The apparatus further comprises means for evaluating the signals including a source of reference signals which denote at least one limit of the range of acceptable densities and means for comparing the density signals with the reference signals, and means for segregating the rod-shaped articles containing stream increments whose densities are outside of the predetermined range from the remaining (acceptable or satisfactory) rod-shaped articles. The surplus removing means of such apparatus is or can be adjustable, and the density monitoring means can further comprise means for pointing at the stream at least one beam of nuclear radiation and a device which generates signals denoting the intensity of nuclear radiation that has penetrated through the stream (or through successive rod-shaped articles). Such apparatus then further comprises means for adjusting the surplus removing means as a function of signals which denote the intensity of nuclear radiation that has penetrated through the stream or through successive rod-shaped articles.

The novel features which are considered as characteristic of the invention are set forth in particular in the appended claims. The improved apparatus itself, however, both as to its construction and its mode of operation, together with additional features and advantages thereof, will be best understood upon perusal of the following detailed description of certain specific embodiments with reference to the accompanying drawing.

BRIEF DESCRIPTION OF THE DRAWING

FIG. 4a is an enlarged view of a detail in the apparatus of FIG. 3 and illustrates the manner of testing discrete rod-shaped articles with a density monitoring device embodying a source of nuclear radiation;

FIG. 4b illustrates the structure of FIG. 4a in a calibrating device for the electrical components of the apparatus;

FIG. 5 is a schematic view of a density monitoring device which is designed to ascertain the density of successive increments of a moving stream of fibrous material by passing radiation through the conveyor for the stream;

DESCRIPTION OF THE PREFERRED EMBODIMENTS

Figure 1:
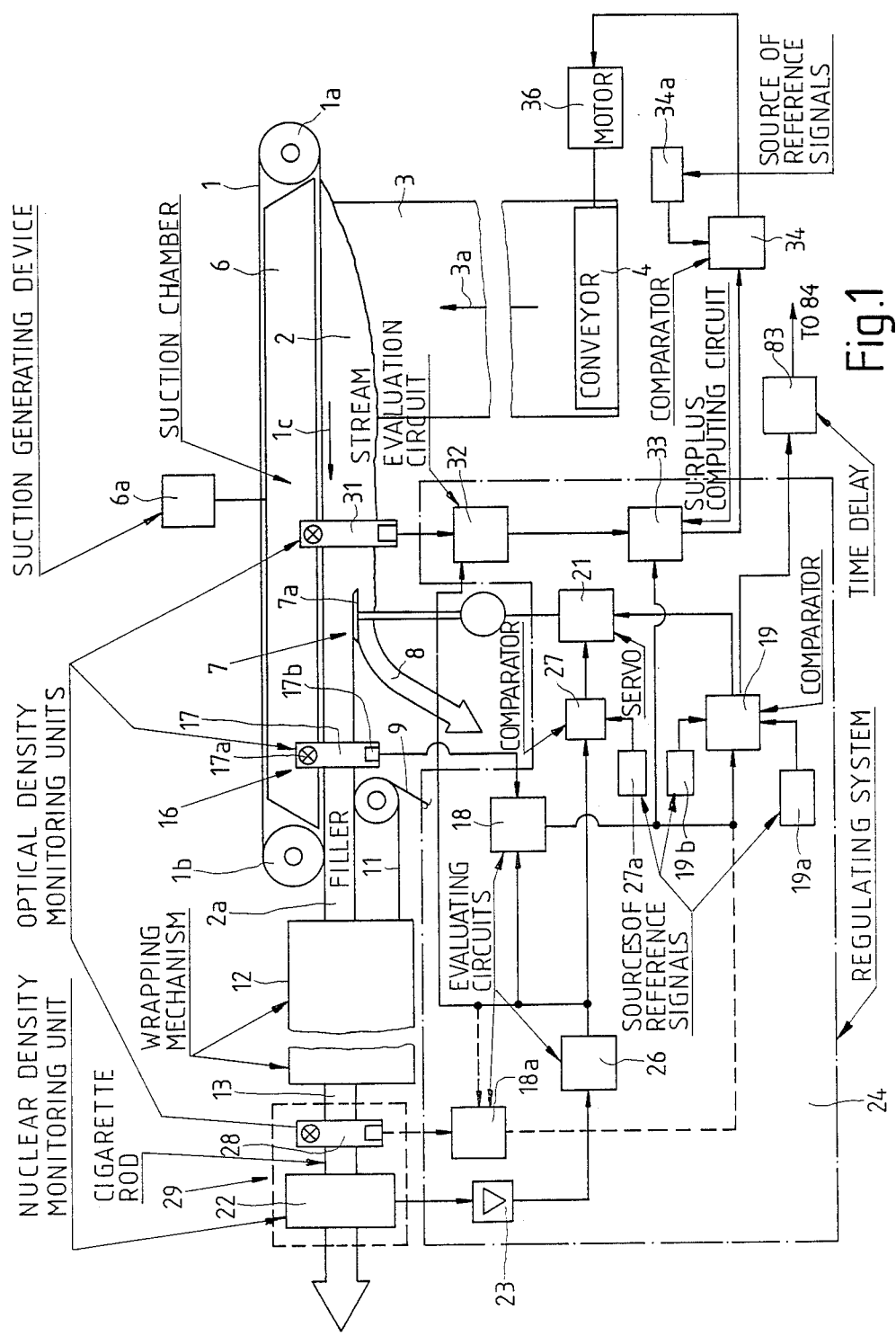
FIG. 1 is a diagrammatic elevational view of an apparatus which embodies one form of the invention and is designed to form and process in a cigarette maker a single continuous stream of fibrous material in accordance with the improved method.

FIG. 1 shows a portion of a cigarette rod making machine wherein a single stream 2 of tobacco particles is continuously formed or built at the underside of the lower reach of an endless air-permeable belt conveyor 1 and is transported in a predetermined direction (arrow 1c) along a substantially horizontal path. FIG. 1 illustrates only those parts of the cigarette rod making machine which are necessary for a full understanding of the invention which resides in the provision of means of processing the stream 2 including means for ascertaining the density and other variable characteristics of the stream as well as means for influencing the making and/or other treatment of the stream in response to signals which are generated by several density monitoring units.

The conveyor 1 is trained over pulleys 1a, 1b one of which is driven by a suitable prime mover (not shown) so as to advance the lower reach of the conveyor in the direction of arrow 1c. Such lower reach travels beneath the foraminous bottom wall of an elongated suction chamber 6 whose outlet is connected with the intake of a fan 6a or another suitable suction generating device. The means for supplying fibrous material (such as fragments of tobacco leaves and/or particles of reconstituted and/or artificial tobacco) includes a duct 3 wherein a shower of fibrous material rises in the direction of arrow 3a under the action of suction in the chamber 6 and/or under the mechanical action of a rotary roller- or drum-shaped conveyor 4 driven by a variable-speed motor 36 and serving to propel the particles of the shower toward and into the stream growing or forming station at the upper end of the duct 3. The means for causing the shower of fibrous material to rise in the duct 3 can further comprise one or more nozzles (not shown) which discharge jets of compressed air or another gaseous fluid toward the inlet at the lower end of the duct 3. Reference may be had to numerous United States and foreign patents of the assignee wherein the construction of means for delivering fibrous material to a stream forming or building station are shown and described in full detail.

The apparatus of FIG. 1 further comprises a trimming or equalizing device 7 having means 7a for removing at least some of the surplus 8 from the stream 2 at the underside of the lower reach of the conveyor 1. Such stream is caused to adhere to the underside of the lower reach of the conveyor 1 due to the establishment of a pressure differential by the suction chamber 6 and suction generating device 6a. The surplus removing means 7a can include two coplanar discs (only one shown) and a motor-driven brush or milling tool (not shown) which latter serves to remove that portion (8) of the stream 2 that extends downwardly beyond the common plane of the discs. The trimming or equalizing device 7 is adjustable in that its surplus removing means 7a is movable up and down to assume any one of several positions at different levels below the lower reach of the conveyor 1 and to thus determine the quantity of fibrous material in the trimmed or equalized stream 2a (hereinafter called filler for short) which is advanced by the conveyor 1 beyond the surplus removing station. The latter is located in a predetermined portion of the path which is defined by the conveyor 1 and by a further conveyor 11 (known as garniture belt) which is located downstream of the conveyor 1 (as seen in the direction of arrow 1c).

Figure 6:
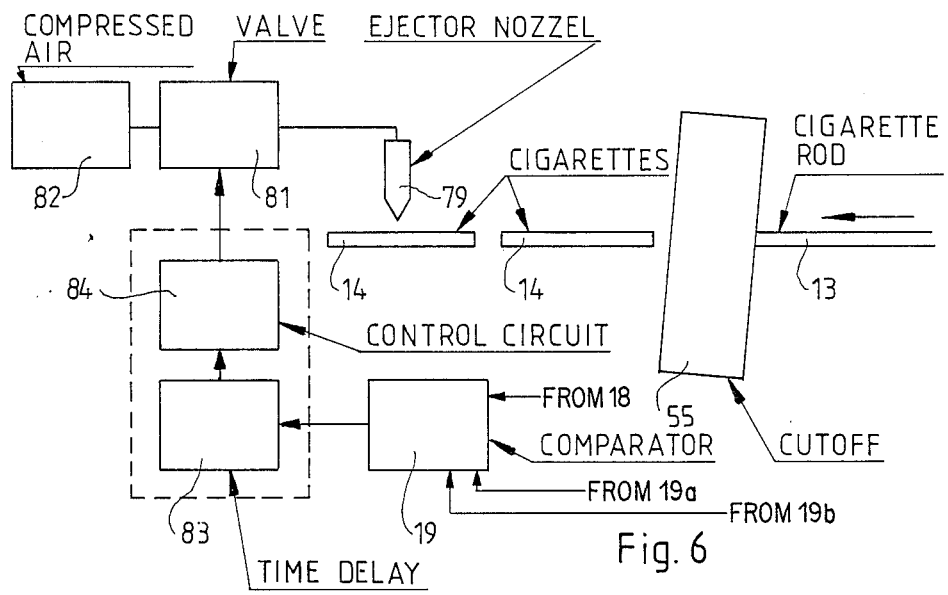
FIG. 6 is a diagrammatic view of devices for subdividing a stream into rod-shaped articles of desired length and for segregating defective rod-shaped articles from satisfactory articles.

The rod making machine further comprises a source (such as a replaceable reel, not shown) of a web or strip 9 of wrapping material (normally cigarette paper) which is draped around successive increments of the filler 2a during travel with the upper reach of the garniture belt 11 through a conventional wrapping mechanism 12 of known design. Reference may be had to numerous United States and foreign patents of the assignee of the present application, for example, to those which describe the so-called PROTOS cigarette rod making machine. The wrapping mechanism 12 is normally designed to convert the web 9 (one marginal portion of which is coated with a film of suitable adhesive) into a tube which surrounds the filler 2a and wherein the one marginal portion is folded over and is caused to adhere to the other marginal portion so that the two marginal portions jointly form a seam which extends in parallelism with the axis of the resulting continuous cigarette rod 13. The latter consists of the filler 2a (i.e., of the equalized stream 2) and of a tube or envelope constituting the converted cigarette paper web 9. The quantity of fibrous material per unit length of the rod 13 is determined by the density of the stream 2 and by the selected distance of the surplus removing means 7a from the lower each of the conveyor 1. The cigarette rod 13 is thereupon caused to pass through a subdividing or severing device in the form of a cutoff 55 (see FIG. 6) to yield a file of discrete rod-shaped articles 14 each of which constitutes a plain cigarette of unit length or multiple unit length. Defective articles 14 are segregated from satisfactory articles in a manner to be described in connection with FIG. 6, and the satisfactory articles are introduced into a filter tipping machine to be assembled with filter rod sections into filter cigarettes of unit length or multiple unit length. Alternatively, satisfactory rod-shaped articles 14 can be delivered directly to the magazine of a packing machine or into a reservoir (e.g., a first-in last-out reservoir known as RESY which is distributed by the assignee of the present application) for temporary storage prior to admission into a filter tipping machine or into a packing machine.

The apparatus in the cigarette rod making machine of FIG. 1 further comprises means for monitoring the density of the stream 2 and/or filler 2a and/or cigarette rod 13 and/or rod-shaped articles 14. The density monitoring means 16 comprises a density monitoring unit 17 which is located immediately or closely downstream of the trimming device 7 (as seen in the direction of arrow 1c) and includes a suitable source 17a of optical radiation serving as a means for directing or pointing at least one beam of optical radiation against or at successive increments of the moving filler 2a so that the intensity of optical radiation which has penetrated through the filler 2a is indicative of the density of the respective increments of the filler. The unit 17 further includes a transducer 17b which constitutes a device for generating signals denoting the intensity of optical radiation which has penetrated through the filler 2a. The interval of time which elapses between the removal of surplus from an increment of the stream 2 and the monitoring of optical radiation which has penetrated through such increment is extremely short (in the range of a few milliseconds).

The output of the transducer 17b of the density monitoring unit 17 is connected to one input of an evaluating circuit 18 wherein the incoming signals are converted into signals directly denoting the density of the respective increments of the filler 2a (equalized stream 2). The output of the evaluating circuit 18 transmits successive density signals to a comparator circuit 19 wherein the density signals are compared with a reference signal supplied by an adjustable potentiometer 19a or another suitable source of reference signals. The output of the comparator circuit 19 transmits appropriate signals when the intensity and/or other parameters of density signals supplied by the evaluating circuit 18 deviate from the intensity and/or other parameters of the reference signal from the source 19a so that the level of the surplus removing means 7a is then changed and the latter increases or reduces the quantity of surplus 8 which is being removed from the stream 2 in order to convert the latter into the filler 2a. The means for adjusting the level of the surplus removing means 7a includes a reversible servomotor 21 or another suitable adjusting unit whose input is connected with the output of the comparator circuit 19 and whose output is connected to the mechanism for moving the surplus removing means 7a up or down. The exact design of the parts of the servomotor 21 and of the means for transmitting motion between the servomotor and the surplus removing means 7a are well known in the art of cigarette making and need not be described here.

The just described system for regulating the rate of removal of surplus 8 from the stream 2 operates quite satisfactorily as long as density is the only variable characteristic of the stream 2. However, the stream 2 often exhibits two or more variable characteristics, especially density, color and blend (i.e., the rate at which two or more different tobacco types are mixed to form the stream 2). It has been found that the intensity of optical radiation which penetrates through the filler 2a is influenced not only by the density of the filler but also by the color of its fibrous material and/or by the blend of tobacco particles which form the stream 2 and filler 2a. Thus, the utilization of density monitoring unit 17 with its source or sources 17a of optical radiation and its transducer or transducers 17b is amply sufficient if the color and/or blend of the constituents of the stream 2 is not expected to change. However, such density measurement is likely to furnish distorted signals, which are not truly indicative of the density of successive increments of the filler 2a, if the duct 3 does not supply an unchanging mixture or fibrous material, i.e., if the shower which rises in the direction of arrow 3a does not contain a single type of tobacco (such as burley or oriental or a constant mixture of the two) so that the color of a first length of the filler 2a deviates from the color of the next-following length of the filler and/or if the composition of a first length of the filler deviates from that of the next-following length.

In order to ensure that the adjusting means 21 for the surplus removing means 7a can select the level of the latter without being adversely influenced by changes of the color and/or composition of the filler 2a, the density monitoring means 16 of the apparatus in the cigarette rod making machine of FIG. 1 further comprises a second density monitoring unit 22 which is adjacent the path of the filler 2a downstream of the unit 16 and includes a source 22a (FIG. 2) of corpuscular (nuclear) radiation or a source of X-rays aimed or pointed at the cigarette rod 13, and a transducer (such as an ionization chamber 22b shown in FIG. 2) which ascertains the intensity of nuclear radiation or X-rays that has or have penetrated through successive increments of the rod 13 (i.e., through successive increments of the equalized and draped stream 2). The signals at the output of the transducer 22b are transmitted to an amplifier 23 which transmits amplified signals to an evaluating circuit 26 wherein such signals are converted into signals denoting the density of successive increments of the filler 2a in the cigarette rod 13. The intensity of the beam of nuclear radiation which penetrates through the rod 13 and impinges upon the transducer 22b is not affected by the color and/or blend of the fibrous material forming the filler 2a, i.e., nuclear radiation is influenced by changes of color and/or blend in a manner which is substantially different from the manner in which the color and/or blend of the constituents of the filler 2a influences the beam of optical radiation that penetrates across the filler 2a between the radiation source or sources 17a and the transducer or transducer 17b.

The output of the evaluating circuit 26 is connected with a second input of the evaluating circuit 18 wherein the density signals which are obtained as a result of optical density measurement at 17 are modified by density signals which are obtained as a result of nuclear density measurement of the draped filler 2a at 22. Consequently, those signals which the evaluating circuit 18 transmits to the comparator circuit 19 are at least substantially devoid of the influence of color and/or blend of the stream 2 upon the density measurement which is carried out by the optical density monitoring unit 17. In other words, the determination of density by the unit 17 (as influenced by signals from the evaluating circuit 26) is reliable irrespective of whether the color and/or blend of the stream 2 and filler 2a remains constant. Otherwise stated, the rate at which the means 7a of the trimming device 7 removes surplus 8 from the stream 2 is dependent solely on the density of successive increments of the filler 2a, and such rate can be changed instantaneously if the monitored density (denoted by the signal from the evaluating circuit 18 to the comparator circuit 19) deviates from a desirable or optimum density (as denoted by the reference signal or signals from the source 19a).

FIG. 1 shows that the output of the evaluating circuit 26 is further connected with one input of a comparator circuit 27 another input of which is connected with a source 27a (e.g., an adjustable potentiometer) of reference signals denoting the desired or optimum density of successive increments of the draped filler 2a (i.e., of successive increments of the cigarette rod 13). If the signals which are transmitted by the circuit 26 deviate from signals which are transmitted by the source 27a of reference signals, the output of the comparator circuit 27 transmits a signal to the servomotor (adjusting means) 21 for the surplus removing means 7a of the trimming device 7 so that the level of the surplus removing means 7a is determined by signals from the comparator circuit 19 as well as by signals from the comparator circuit 27.

The adjustment of the level of surplus removing means 7a in response to signals from the comparator circuit 27 takes place with a certain delay (as compared with the adjustment in response to signals from 19) because the distance of the density monitoring unit 22 from the trimming station exceeds the distance of such station from the density monitoring unit 17. This is the reason that the adjustment of the level of surplus removing means 7a under the action of signals from the evaluating circuit 18 is superimposed upon the adjustment under the action of signals from the evaluating circuit 26 in order to make sure that the rate of surplus removal will be altered practically without any delay (under the action of signals from the evaluating circuit 18) in response to generation of density signals by the unit 17) but that such rate can also be influenced by signals from the evaluating circuit 26 (and hence independently of eventual changes of the color and/or blend of the filler 2a). Of course, signals which are transmitted by the evaluating circuit 18 are also influenced by signals from the evaluating circuit 26 so as to even more reliably ensure that the level of the surplus removing means 7a will be changed exclusively in response to changes of density of the filler 2a.

If it is not overly important to bring about practically instantaneous changes of the level of surplus removing means 7a in response to changes of density of the filler 2a, the optical density monitoring unit 17 can be replaced with a similar or identical optical monitoring unit 28 which is placed adjacent the path of the cigarette rod 13, e.g., into close or immediate proximity of the nuclear density monitoring unit 22. The adjustment of the level of surplus removing means 7a in response to changes of density (as detected by the unit 28) is then delayed (as compared with the adjustment in response to signals from the unit 17) because the unit 28 is more distant from the surplus removing station. However, each of the units 17, 28 exhibits the advantage that it allows for the utilization of a nuclear density monitoring unit 22 which employs a rather weak source (22a) of nuclear radiation or X-rays. This is due to the fact that signals which are generated by the unit 22 are used solely to correct or modify signals which are generated by the unit 17 or 28, i.e., to ensure that signals which denote optical density measurements and are transmitted to the servomotor 21 are not influenced by changes of variable characteristics other than density of the filler 2a. If desired, the density monitoring units 22 and 28 can be assembled into a composite density monitoring arrangement 29 which is indicated in FIG. 1 by broken lines. This facilitates the installation of the units 22, 28 or removal of the units 22, 28 from the cigarette rod making machine.

The optical density monitoring units 17 and 28 can be used simultaneously or interchangeably. Thus, and as shown in FIG. 1 by broken lines, the regulating system 24 of the cigarette rod making machine can comprise a third evaluating circuit 18a which has a first input connected with the output of the transducer in the optical density monitoring unit 28 and a second input connected with the output of the evaluating circuit 26. The output of the evaluating circuit 18a is connected with the output of the evaluating circuit 18, and more specifically with the density signal receiving input of the comparator circuit 19.

FIG. 1 further shows a third optical density monitoring unit 31 which is adjacent the path of the untrimmed stream 2 ahead of the station for the surplus removing means 7a (as seen in the direction of arrow 1c) and serves to generate signals denoting the intensity of optical radiation which is aimed at the stream 2 by the optical radiation source of the unit 31. Such intensity is determined by the transducer of the unit 31, and this transducer transmits appropriate signals to an evaluating circuit 32 which further receives modifying signals from the evaluating circuit 26 (i.e., indirectly from the nuclear density monitoring unit 22). The output of the evaluating circuit 32 transmits signals to a surplus computing circuit 33 which further receives signals from the output of the evaluating circuit 18 so that it can compare signals which are generated by the optical density monitoring units 17, 31 downstream and upstream of the surplus removing or equalizing station. This enables the computing circuit 33 to transmit signals which are indicative of the quantity of the removed surplus 8 of fibrous material. The surplus computing circuit 33 is or can constitute a differentiating circuit of any known design. The difference between the intensities of signals from 18 and 32 is indicative of the quantity of the removed surplus 8, and the corresponding signal is transmitted from the surplus computing circuit 33 to a comparator circuit 34 wherein the signal is compared with a reference signal supplied by a source 34a of reference signals which denote the desired or optimum quantity of removed surplus. If the intensity and/or one or more additional parameters of the signal which is transmitted by the circuit 33 deviate from the reference signal which is transmitted by the source 34a, the comparator circuit 34 transmit a signal to the controls of the aforementioned variable-speed motor 36 which increases or reduces the RPM of the material feeding conveyor 4 so that the quantity of fibrous material which enters the duct 3 per unit of time is increased or reduced, depending upon whether the quantity of removed surplus 8 is insufficient or excessive.

It will be seen that the regulating system 24 of FIG. 1 allows for direct determination of the quantity of removed surplus 8 of fibrous material and for immediate corrective undertakings if the quantity of the removed surplus is unsatisfactory, i.e., if such quantity deviates from that determined by the intensity and/or other parameters of the reference signal which is transmitted by the source 34a. It is clear that the signal which is transmitted by the output of the comparator circuit 34 can influence one or more nozzles which discharge compressed air to regulate the rate of admission of fibrous material into the duct 3 and/or any other means capable of influencing the quantity of fibrous material which is supplied into the stream building zone above the duct 3 per unit of time. All that counts is to ensure that the rate of feed of fibrous material into the stream forming zone is altered when the signal from the surplus computing circuit 33 denotes that the rate of surplus removal from the stream 2 is unsatisfactory.

The establishment of a signal transmitting connection between the evaluating circuit 26 for density signals which are generated by the nuclear density monitoring unit 22 and the evaluating circuit 32 for signals from the transducer of the optical density monitoring unit 31 constitutes an optional but desirable feature of the improved apparatus. Such connection ensures that the signals from the transducer of the monitoring unit 31 are modified so as to at least substantially eliminate therefrom the influence of changes of color and/or blend of the stream 2. This further enhances the accuracy of determination of the quantity of fibrous material which forms the removed surplus 8.

An important advantage of the optical density monitoring unit 17 is that it is located immediately or closely downstream of the station (for the adjustable surplus removing means 7a) where the density of the stream 2 undergoes a pronounced change as a result of removal of the surplus 8. This allows for a shortening of the interval which elapses between the determination of modified density (namely the determination of density of the filler 2a) and the last influencing of the density (by the surplus removing means 7a). Therefore, the number of defective increments of the filler 2a between the surplus removing means 7a and the unit 17 (and the percentage of defective rod-shaped articles 14) can be reduced to a minimum because the signals from the transducer 17b of the unit 17 are used to adjust the surplus removing means 7a when such adjustment is warranted in view of detected unsatisfactory density of the monitored increment or increments of the filler 2a. Since the components (17a, 17b) of the unit 17 are or can be very small, the unit 17 can be placed into immediate or very close proximity of the surplus removing means 7a. The same applies for the optical density monitoring unit 31. In addition, the utilization of relatively small optical density monitoring units renders it possible to place a large number of such units next to selected portions of the path for the stream 2, filler 2a, draped filler or rod 13 and/or rod-shaped articles 14 which are obtained as a result of subdivision of the rod 13 without in any way interfering with normal operation of the cigarette rod making machine.

The feature that signals from the optical density monitoring unit 17, 28 and/or 31 are modified by signals from the nuclear density monitoring unit 22 and that signals from one or more optical density monitoring units (such as 17 and 28) are used to adjust the surplus removing means 7a of the trimming device 7 ensures that the surplus removing means 7a is or can be adjusted with a minimum of delay following detection of an unsatisfactory increment of the stream and that signals from the optical density monitoring unit or units are modified by signals from the unit 22 in order to ensure that the surplus removing means 7a is adjusted exclusively in response to deviations of density from an acceptable range of densities but that such adjustment is not influenced (or is not unduly influenced) by other variable characteristics of the stream which are likely to distort the signals from optical density monitoring units.

Figure 2:
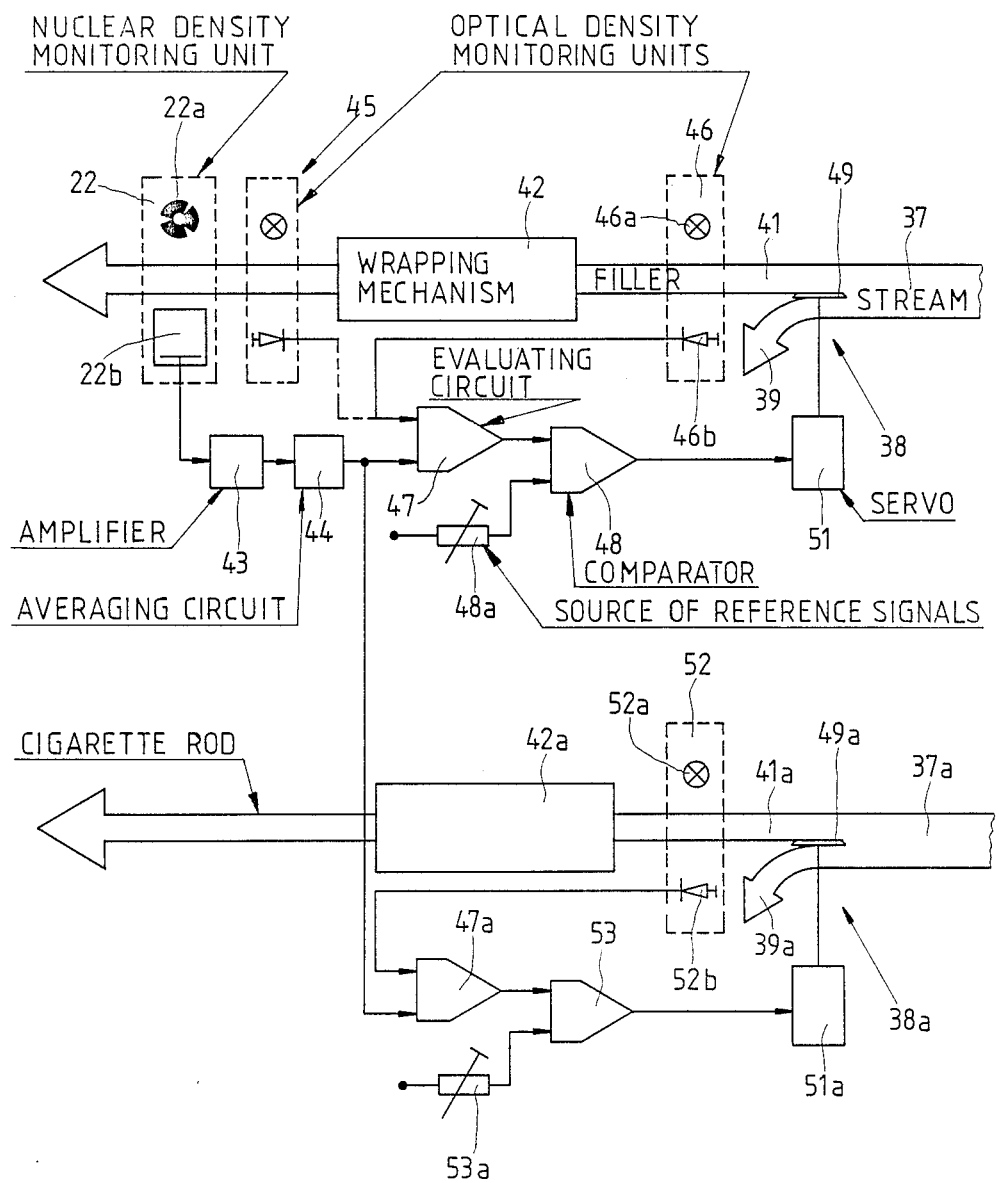
FIG. 2 is a diagrammatic view of a portion of a modified apparatus which is designed to simultaneously form and process two streams of fibrous material.

FIG. 2 shows a modified apparatus which is installed in a machine for simultaneous forming and processing of several tobacco streams including a first stream 37 and a second stream 37a. The conveyors (not specifically shown) which are used to transport the streams 37, 37a along discrete paths (which may but need not be parallel to each other) can be identical with or analogous to the conveyor 1 of the apparatus of FIG. 1. For the sake of clarity and simplicity, FIG. 2 merely shows those parts of the modified rod haking machine and those parts of the modified apparatus which are necessary for full understanding of the invention. The apparatus preferably comprises a single distributor (also called hopper) which contains a source of fibrous material, and means for supplying fibrous material from the source to stations for the formation or building of the streams 37 and 37a. Such material supplying means can comprise a discrete duct (3) for each of the streams and a discrete variable-speed material propelling conveyor (4) for each of the ducts. Reference may be had, for example, to commonly owned U.S. Pat. No. 4,185,644 to Heimann et al. which shows a distributor or hopper and means for supplying fibrous material from the magazine of such distributor to a single stream forming station.

Each of the streams 37, 37a carries a surplus (39, 39a) of fibrous material which is removed by a discrete trimming or equalizing device (38, 38a) comprising adjustable surplus removing means (49, 49a) which may but need not be identical with the surplus removing means 7a in the apparatus of FIG. 1. The trimmed or equalized streams 37, 37a respectively constitute fillers 41, 41a which are draped into discrete webs or strips (not shown) of cigarette paper or other suitable wrapping material in discrete wrapping mechanisms 42, 42a to be converted into discrete cigarette rods each of which is thereupon subdivided to yield a file of discrete rod-shaped articles of unit length or multiple unit length, e.g., a file of plain cigarettes of unit length which are ready for admission into a reservoir or directly into a packing machine. Plain cigarettes of double unit length can be admitted into a reservoir or directly into a filter tipping machine, e.g., a machine known as MAX S which is distributed by the assignee of the present application.

The density of successive increments of the filler 41 in the cigarette rod which issues from the wrapping mechanism 42 is monitored by a nuclear density monitoring unit 22 which is or can be identical with the similarly referenced unit of FIG. 1 and includes a source 22a of nuclear radiation (e.g., X-rays or beta rays) and a transducer in the form of an ionization chamber 22b having its output connected with a logarithmic amplifier 43 for signals denoting the intensity of nuclear radiation that has penetrated across the filler 41 of the cigarette rod issuing from the wrapping mechanism 42. The output of the logarithmic amplifier 43 is connected with the input of an averaging circuit 44 whose output transmits a signal denoting the average intensity of a selected number of successively generated signals denoting the intensity of nuclear radiation that has penetrated through the filler 41.

The apparatus which embodies the structure of FIG. 2 further includes an optical density monitoring unit 46 (indicated by broken lines) which is installed adjacent the path of the filler 41 immediately or closely downstream of the trimming or equalizing device 38 and has one or more sources 46a of optical radiation which is pointed or aimed at the filler 41. The intensity of optical radiation (such as infrared light) which has penetrated through successive increments of the moving filler 41 is ascertained by one or more photoelectronic transducer 46b serving to transmit corresponding signals to one input of an evaluating circuit 47 another input of which receives signals from the averaging circuit 44. The output of the evaluating circuit 47 transmits signals which denote the density of successive increments of the filler 41 immediately downstream of the trimming unit 38, and such signals are modified by signals from the averaging circuit 44 so that they are not appreciably influenced by eventual changes of color and/or blend of the stream 37. The thus modified density signals are transmitted to one input of a comparator circuit 48 another input of which receives reference signals from an adjustable potentiometer 48a or another suitable source of signals denoting the desired density of the filler 41. If the signals which are transmitted by the circuit 47 deviate from signals which are supplied by the source 48a, the comparator circuit 48 transmit signals to a servomotor 51 which serves as a means for changing the level of the surplus removing means 49, i.e., for adjusting the rate of removal of surplus 39 from the stream 37.

If it is not overly important to determine the density of successive increments of the filler 41 immediately downstream of the trimming device 38, the apparatus of FIG. 2 can comprise an optical density monitoring unit 45 which is adjacent the path of movement of the cigarette rod issuing from the wrapping mechanism 42, e.g., closely or immediately adjacent the nuclear density monitoring unit 22. As shown by broken lines, the output(s) of the transducer(s) of the optical density monitoring unit 45 is(are) connected to that input of the evaluating circuit 47 which serves to receive optically determined density signals (from the unit 45 and/or 46).

The density of successive increments of the filler 41a is monitored by an optical density monitoring unit 52 having one or more sources 52a of optical radiation which is aimed at the filler 41a. The intensity of optical radiation which has penetrated through the filler 41a is monitored by one or more transducers 52b whose output or outputs are connected with one input of an evaluating circuit 47a. The other input of the evaluating circuit 47a is connected with the output of the averaging circuit 44. The output of the evaluating circuit 47a transmits signals which denote the density of successive increments of the filler 41a and are no longer influenced by variations of color and/or blend of the stream 37a. While it is possible to provide a discrete nuclear density monitoring unit (corresponding to the unit 22) adjacent the path of the cigarette rod which issues from the wrapping mechanism 42a, such second nuclear density monitoring unit is not necessary if the streams 37, 37a are formed from fibrous material which is being withdrawn from a common magazine.

The output of the evaluating circuit 47a is connected with one input of a comparator circuit 53 another input of which receives reference signals from a source 53a, such signals denoting the desired density of the filler 41a. If the actual density deviates from the desired density, the output of the comparator circuit 53 transmits a signal to an adjusting means 51a (e.g., a reversible servomotor) which can change the level of the surplus removing means 49a in the trimming device 38a so that the quantity of fibrous material forming the surplus 39a is increased or reduced depending on the intensity of signals which are transmitted by the output(s) of the transducer(s) 52b.

An advantage of the apparatus which is shown in FIG. 2 is that a single nuclear density monitoring device 22 (which employs a weak source (22a) of nuclear radiation) suffices to properly modify signals from the transducer 46b and 52b. This reduces the cost of the apparatus because it is not necessary to multiply the precautionary undertakings which are required in connection with each source of nuclear radiation. Moreover, the utilization of a single relatively weak source (22a) of nuclear radiation renders it possible to rely on relatively simple and less expensive means for shielding the attendants from such radiation. In other words, savings are achieved because the apparatus employs a single nuclear density monitoring unit as well as because the single nuclear density monitoring unit can embody a relatively weak source of nuclear radiation. The single nuclear density monitoring unit 22 is optional but desirable and advantageous because it enables the evaluating circuits 47 and 47a to transmit optically determined density signals which are not influenced at all, or are not unduly influenced, by eventual further variable characteristics (color and/or blend) of the streams 37 and 37a.

Figure 3:
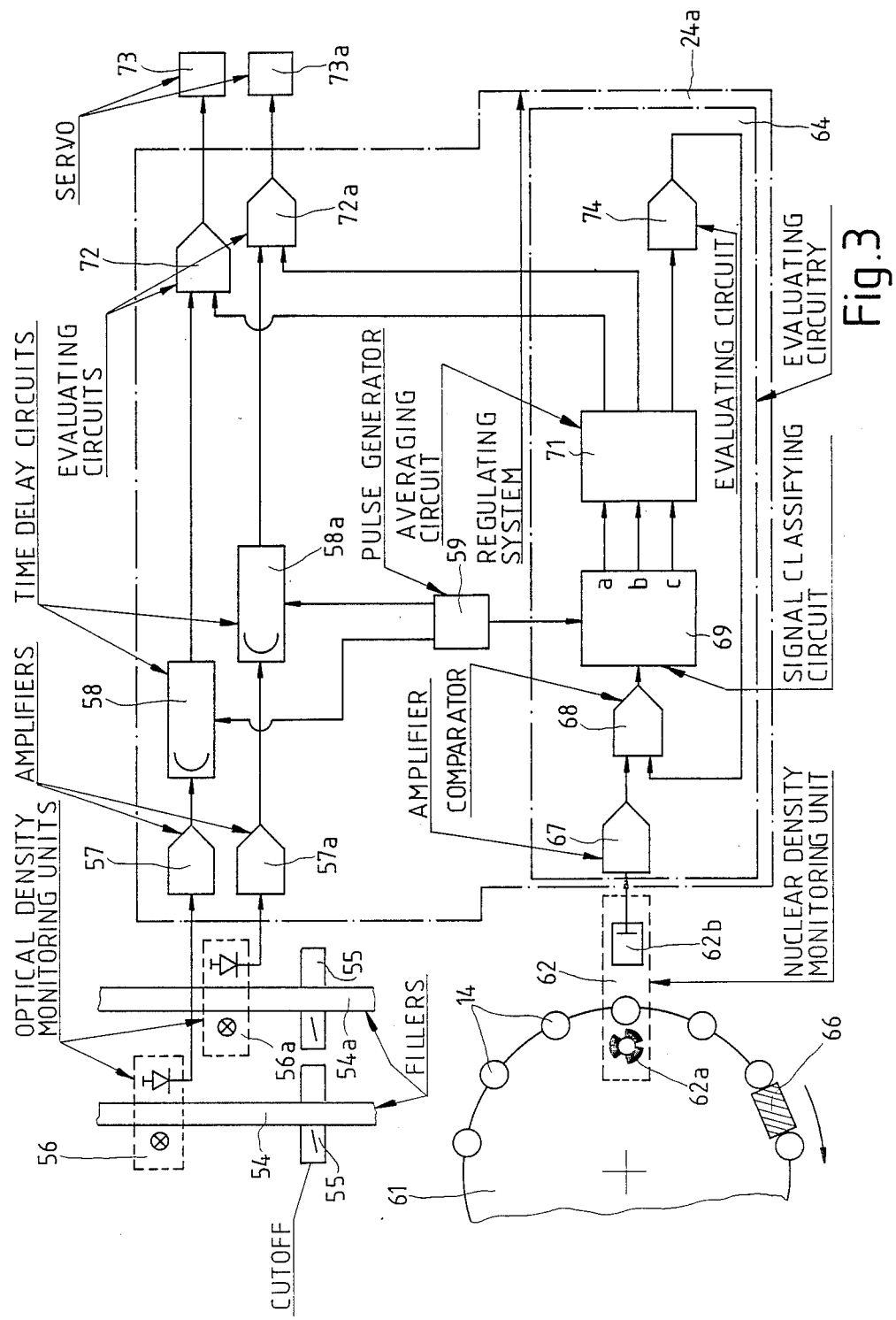
FIG. 3 is a diagrammatic view of an apparatus constituting a modification of the apparatus which is shown in FIG. 2.

FIG. 3 shows a portion of an apparatus which constitutes a modification of the apparatus of FIG. 2 and is also installed or embodied in a machine for the making of two streams of fibrous material. The upper left-hand portion of FIG. 3 merely shows two fillers 54, 54a which constitute trimmed streams of fibrous material and each of which can be formed in the same way as described in connection with FIG. 2, i.e., by conveying two discrete streams along separate paths and by removing surplus from each of the streams with a discrete adjustable trimming or equalizing device. The fillers 54, 54a are thereupon draped into discrete webs or strips of cigarette paper or other suitable wrapping material, and the resulting cigarette rods are subdivided so that each rod yields a series of discrete rod-shaped articles 14 (such as plain cigarettes, cigarillos, cigars or cheroots of unit length or multiple unit length).

The densities of the fillers 54, 54a are respectively determined by optical density monitoring units 56 and 56a each of which can be identical with any one of the previously described optical density monitoring units (e.g., with the unit 45, 46 or 52 of FIG. 2). The transducers of the density monitoring units 56, 56a are respectively connected to the inputs of discrete logarithmic amplifiers 57, 57a which transmit amplified and logarithmed density signals to discrete time delay units 58, 58a (e.g., in the form of shift registers) which receive signal advancing pulses from a timing pulse generator 59.

The rod-shaped articles 14 which are obtained as a result of regular severing or subdivision (at 55) of the draped fillers 54, 54a at first move axially in the form of single files but are preferably caused to thereupon advance sideways (i.e., at right angles to their respective longitudinal axes), preferably as a result of introduction into successive axially parallel peripheral flutes of one or more rotary drum-shaped conveyors 61 one of which is shown in the lower left-hand portion of FIG. 3. The arrangement is or can be such that a first conveyor 61 is provided for articles 14 which are obtained as a result of subdivision of the draped filler 54, and a second conveyor 61 is provided for articles 14 which are obtained as a result of subdivision of the draped filler 54a. Each of the conveyors 61 can deliver articles 14 (e.g., plain cigarettes of unit length or multiple unit length) to a discrete filter tipping machine, to a discrete reservoir or to a discrete packing machine. The flutes at the periphery of the conveyor 61 which is shown in FIG. 3 are in communication with suction ports (not specifically shown) in a manner which is customary in connection with the transport of rod-shaped articles in machines of the tobacco processing industry so as to ensure that the articles 14 are held in the respective flutes against any axial and/or other stray movements during transport past a nuclear density monitoring unit 62 having a source 62a of nuclear radiation which is aimed at successive rod-shaped articles 14 and a transducer 62b (e.g., an ionization chamber) which transmits signals denoting the intensity of nuclear radiation which has penetrated through successive articles 14 on the rotating conveyor 61. If the fillers 54, 54a are made of fibrous material which is drawn from a single source, it suffices to provide a single nuclear density monitoring unit 62 which is placed adjacent the path of movement of successive rod-shaped articles 14 with one of the rotary drum-shaped conveyors 61.

FIG. 4a shows that a portion of each rod-shaped article 14 projects beyond one axial end of the respective flute in the conveyor 61 and that the nuclear density monitoring unit 62 employs a U-shaped carrier one leg of which supports the radiation source 62a and the other leg of which supports the transducer 62b. The projecting (unsupported) portions of successive articles 14 pass through the gap 63 between the source 62a and transducer 62b so that the latter can transmit to an evaluating circuit 64 signals which are indicative of the intensity of nuclear radiation that has penetrated through successive articles 14. The evaluating circuit 64 for signals from the transducer 62b is also shown in FIG. 3 (by phantom lines).

FIGS. 3 and 4b show that the drum-shaped conveyor 61 carries a calibrating element 66 in the form of a diaphragm which projects beyond one axial end of the conveyor 61 so that it enters the gap 63 between the radiation source 62a and the transducer 62b for a short interval of time during each revolution of the conveyor 61. FIG. 4b shows the diaphragm 66 in the gap 63 so that nuclear radiation which issues from the source 62a must penetrate through the diaphragm 66 in order to reach the transducer 62b. This diaphragm has a predetermined transmissivity to nuclear radiation and is used in order to allow for regular calibration of the evaluating circuit 64 in the regulating system 24a of FIG. 2 and/or for regular determination of the accuracy of the nuclear density monitoring unit 62 and/or the extent of deviation of density of successive rod-shaped articles 14 on the conveyor 61 from an optimum density.

As shown in FIG. 3, the evaluating circuit 64 comprises a logarithmic amplifier 67 whose input is connected to and receives signals from the transducer 62b of the nuclear density monitoring unit 62. The output of the amplifier 67 transmits logarithmed and amplified signals to a comparator circuit 68 wherein signals denoting the density of successive rod-shaped articles 14 are compared with signals which are transmitted by the transducer 62b when the diaphragm 66 is located in the gap 63 of the unit 62 (FIG. 4b). The output of the comparator circuit 68 is connected with one input of a signal classifying or allotting circuit 69 having another input which is connected with an output of the timing pulse generator 59. The circuit 69 discriminates between (a) signals which are generated as a result of the monitoring of rod-shaped articles 14 obtained from the filler 54, (b) signals which are generated as a result of the monitoring of rod-shaped articles 14 obtained from the filler 54a (it being assumed that the conveyor 61 transports all of the rod-shaped articles 14), and (c) signals which are generated as a result of monitoring of the predetermined density or transmissivity of the diaphragm 66. The correspondingly referenced outputs of the circuit 69 transmit signals to an averaging circuit 71 whose outputs are respectively connected with evaluating circuits 72, 72a and 74. The circuit 71 separately averages predetermined numbers of successive signals from the outputs a, b and c of the classifying circuit 69.

The evaluating circuit 72 processes signals from the time delay circuit 58 and averaging circuit 71 and transmits signals to a servomotor 73 serving as a means for adjusting the surplus removing means (not shown) for the stream of fibrous material which is converted into the filler 54. The circuit 58 delays the signals from the optical density monitoring unit 56 for an interval of time corresponding to that which elapses while the monitored increment of the filler 54 (i.e., the corresponding rod-shaped article 14) advances toward and reaches the gap 63 in the nuclear density monitoring unit 62. This ensures that the evaluating circuit 72 invariably compares optically and nuclearly determined density signals stemming from the monitoring of one and the same increment of the filler 54. The evaluating circuit 72 modifies the optically determined signals from the time delay unit 58 by nuclearly determined signals from the output a of the classifying circuit 69 to thus ensure that the signals which are transmitted to the servomotor 73 are not influenced by variable characteristics other than densities of the respective increments of the filler 54.

Signals which are transmitted by the output b of the classifying circuit 69 are transmitted by 71 to the corresponding input of the evaluating circuit 72a which further receives properly delayed signals from the time delay circuit 58a to transmit signals for actuation of a servomotor 73a which adjusts the surplus removing means for the stream which is being converted into the filler 54a. Again, signals from the output b of the classifying circuit 69 are utilized to modify corresponding optically determined density signals from the unit 56a to thus ensure that the signals which are used (when necessary) to actuate the servomotor 73a are not influenced by variable characteristics other than density of successively monitored increments of the filler 54a.

The output c of the classifying circuit 69 transmits signals denoting successively ascertained transmissivity of the diaphragm 66 on the conveyor 61; such signals are averaged in the circuit 71 and are transmitted to the evaluating circuit 74 which is a dividing circuit and generates a signal that is the reciprocal of the incoming signal. The output of the evaluating circuit 74 is connected to the corresponding input of the comparator circuit 68.

An advantage of the apparatus of FIGS. 3, 4a and 4b is that the nuclear density monitoring unit 62 ascertains the density of finished or nearly finished articles 14. This enhances the reliability and accuracy of density measurements and the effectiveness of regulation in the event of detected departure of monitored density from a range of acceptable densities.

FIG. 5 shows an optical density measuring unit which can be used in the improved apparatus, for example, as the unit 31 in the apparatus of FIG. 1. The tobacco stream 2 travels with the lower reach of the foraminous conveyor 1 between the sidewalls 76 of the duct 3. The bottom wall 77 of the suction chamber 6 is permeable to air so that suction in the chamber 6 is effective to attract fibrous material which forms the stream 2 to the underside of the lower reach of the conveyor 1. The bottom wall 77 has a window 78 which is permeable to optical radiation (e.g., infrared light) issuing from the radiation source 17a of the unit 31, and a portion of such radiation penetrates across the window 78, through successive increments of the conveyor 1 and through successive increments of the stream 2 prior to reaching the transducer 17b of the unit 31. It will be noted that the components 17a, 17b of the optical density monitoring unit 31 are located at opposite sides of the path for the stream 2 and lower reach of the conveyor 1. This is in contrast to customary ways of installing the components of an optical density monitoring device. Heretofore, one of the components 17a, 17b was installed in one of the sidewalls 76 and the other of these components was installed in the other of the sidewalls 76 so that radiation issuing from 17a was compelled to penetrate only and alone through the stream 2 prior to reaching the transducer 17b. In order to ensure that the conveyor 1 will not unduly affect the density measurement by the unit 31, this conveyor is preferably made of a material which offers little resistance to penetration of optical radiation therethrough. A suitable conveyor 1 can be made of interwoven polyamide filaments. It has been found that such conveyor does not distort the measurements which are carried out by the monitoring unit including the radiation source 17a and transducer 17b of FIG. 5.

The accuracy of optical measurements can be enhanced by placing two or more optical density monitoring units next to each other along the path for the stream 2 and/or for the filler which is obtained in response to removal of surplus from the stream 2. The dimensions of the components 17a, 17b are very small so that optical density monitoring units employing such components take up little room and can be readily installed at any desired location along the path of the stream, filler, wrapped filler and/or discrete rod-shaped articles.

Figure 7:
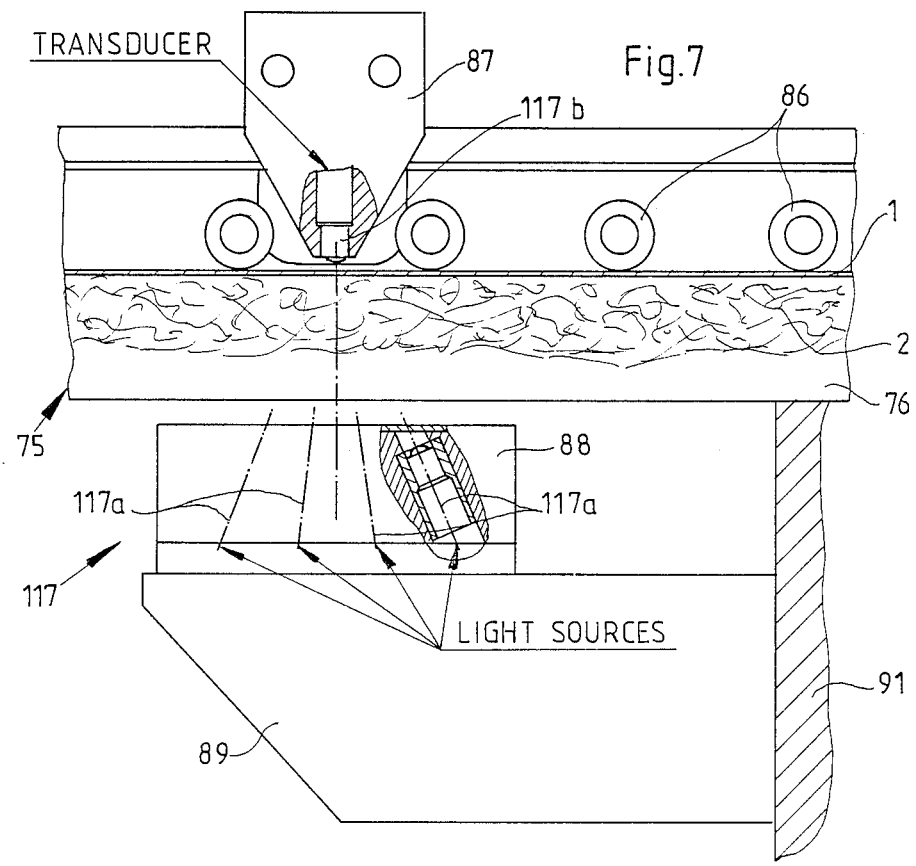
FIG. 7 is a partly elevational and partly sectional view of a portion of the improved apparatus with a modified density monitoring device.

FIG. 7 shows a modified optical density monitoring unit 117 which can be utilized in the apparatus of the present invention. The transducer 117b of this unit is installed in the suction chamber above the lower reach of the foraminous endless belt conveyor 1 which is or can be made of polyamide filaments for reasons described in connection with FIG. 5. The stream 2 advances with the lower reach of the conveyor 1 in an elongated channel 75 having two spaced-apart sidewalls 76 of which only one can be seen in FIG. 7. The lower reach of the conveyor 1 advances along idler rollers 86 which replace the bottom wall 77 and window 78 of FIG. 5 and enable optical radiation issuing from several sources 117a and penetrating through the stream 2 and conveyor 1 to reach the transducer 117b. The latter is mounted on a first support 87, and the radiation sources 117a are mounted on a second support 88 which is secured to a bracket 89 extending from a supporting wall 91 (e.g., a portion of the frame of the rod making machine which embodies the improved apparatus). FIG. 7 shows a single transducer 117b (which is a photoelectronic transducer) and four radiation sources 117 which are suitably inclined relative to each other and each of which can aim or point a beam of optical radiation at the underside of the moving stream 2 so that the radiation which has penetrated through the stream 2 and through the lower reach of the conveyor 1 can impinge upon the transducer 117b.

An advantage of the optical density monitoring unit 117 is that the intensity of radiation (from several sources 117a) which reaches the transducer 117b is sufficiently pronounced to ensure the generation of satisfactory signals. In addition, the sources 117a point or aim radiation at a relatively large portion of the path for the stream 2 which also contributes to more accurate determination of density of successive increments of the stream.

An advantage of optical density monitoring units is that they can readily and reliably detect even relatively small soft spots including actual voids in the stream, filler, wrapped filler or rod-shaped articles as well as portions of the stream, filler, wrapped rod or rod-shaped articles which are much softer (less dense) than the remaining portions and warrant segregation of the respective rod-shaped articles 14 from satisfactory articles. To this end, the apparatus of FIG. 1 comprises a source 19b of reference signals which is connected to the comparator circuit 19. Reference signals from the source 19b denote the lower limit of acceptable densities of increments of the stream 2 and/or filler 2a. If the optically ascertained density of an increment is below the value which is denoted by the reference signal from the source 19b, the rod-shaped article 14 which is to be formed from the corresponding portion of the filler 2a will contain a soft spot and will have to be segregated from the remaining (satisfactory or acceptable) rod-shaped articles. At such time, an output of the comparator circuit 19 transmits a signal to an ejecting device 79 (FIG. 6) which effects segregation of the corresponding article 14 from the path for acceptable articles.

The source 19b can also serve to furnish a reference value denoting the upper limit of acceptable density values so that the ejecting device 79 segregates all rod-shaped articles 14 whose density is below the lower limit or above the upper limit of an acceptable range of densities. Instead of using a more complex source 19b, the comparator circuit 19 can be connected with a first source 19a which transmits signals denoting the lower limit of acceptable densities and with a discrete additional source of reference signals which denote the upper limit of acceptable density values.

The lower output of the comparator circuit 19 which is shown in FIG. 1 transmits signals (denoting unsatisfactory increments of the stream 2 or filler 2a) to a time delay circuit 83 which stores the thus received signal until the rod-shaped article 14 containing the soft spot (namely the soft spot which has induced the comparator circuit 19 to transmit a signal to the time delay circuit 83) to reach the ejecting device 79. The time delay circuit 83 then transmits the signal to a control circuit 84 for a valve 81 in a conduit which connects a source 82 of pressurized fluid (e.g., a source of compressed air) with the ejecting device 79. The latter can constitute a nozzle which discharges one or more streams of pressurized fluid against the oncoming defective rod-shaped article 14 to divert such article from the path for acceptable rod-shaped articles 14, e.g., from the path leading to a reservoir, to a packing machine or to a filter tipping machine. The ejecting station is located downstream of the aforementioned cutoff 55 which subdivides the continuous cigarette rod 13 into a file of discrete rod-shaped articles 14 of unit length or multiple unit length.

If the articles 14 are plain cigarettes which are to be admitted into a filter tipping machine, they are preferably directed into successive axially parallel flutes of a rotary drum-shaped conveyor (similar to the conveyor 61 of FIGS. 3, 4a and 4b) which transports them into or in the filter tipping machine and past the ejecting device 79 so that the latter can expel defective articles 14 from the respective flutes by propelling them axially of the drum-shaped conveyor. Such mode of segregating defective rod-shaped articles from satisfactory rod-shaped articles, which are in random distribution with defective articles, is well known from the art of making cigarettes and analogous rod-shaped articles of the tobacco processing industry.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of our contribution to the art and, therefore, such adaptations should and are intended to be comprehended within the meaning and range of equivalence of the appended claims.

We claim:

1. A method of ascertaining the density of at least one stream of fibrous material of the tobacco processing industry, which in addition to density exhibits at least one further variable characteristic including the color and composition of its constituents, comprising the steps of directing at the stream at least one beam of radiation which is capable of penetrating through the stream whereby the intensity of radiation which has penetrated through the stream denotes the density of the stream, said directing step comprising pointing at the stream at least one beam of a first radiation which is influenced by the at least one further characteristic in a first manner and pointing at the stream at least one beam of a second radiation which is influenced by the at least one further characteristic in a different second manner; and generating at least one density signal which is indicative of said intensity, said generating step including generating at least one first density signal indicative of the intensity of first radiation which has penetrated through the stream and generating at least one second density signal indicative of the intensity of second radiation which has penetrated through the stream.

2. The method of claim 1, further comprising the step of modifying one of said first and second density signals by the other of said first and second signals to at least substantially eliminate the influence of said further characteristic upon one of said modified signals.

3. The method of claim 1, wherein said first radiation is a nuclear radiation.

4. The method of claim 1, wherein said first radiation includes X-rays.

5. The method of claim 1, wherein said second radiation is an optical radiation.

6. The method of claim 5, wherein said optical radiation includes infrared radiation.

7. The method of claim 1, further comprising the steps of forming the stream with a surplus of fibrous material, conveying the stream longitudinally in a predetermined direction along a predetermined path, modifying one of said first and second density signals by the other of said first and second density signals to at least substantially eliminate the influence of said further characteristic upon one of said modified signals, removing the surplus from the stream in a predetermined portion of said path at a rate which is a function of one of said modified signals, and draping the stream into a web of wrapping material in a second portion of said path downstream of said predetermined portion.

8. The method of claim 7, wherein said first radiation is nuclear radiation and said radiation is optical radiation, said second signal being one of said modified signals.

9. Apparatus for processing at least one stream of fibrous material of the tobacco processing industry, which in addition to density exhibits at least one further variable characteristic including the color and composition of its constituents, comprising density monitoring means including means for directing at the at least one stream at least one beam of radiation which is capable of penetrating through the stream whereby the intensity of radiation which has penetrated through the stream denotes the density of the stream, and means for generating at least one density signal which is indicative of said density, said directing means comprising means for pointing at the at least one stream at least one beam of a first radiation which is influenced by the at least one further characteristic in a first manner and means for pointing at the at least one stream at least one beam of a second radiation which is influenced by the at least one further characteristic in a different second manner, said signal generating means comprising a device for generating at least one first density signal indicative of the intensity of first radiation which has penetrated through the stream and a device for generating at least one second density signal indicative of the intensity of second radiation which has penetrated through the stream.

10. The apparatus of claim 9, further comprising means for evaluating said first and second density signals, said evaluating means including means for modifying one of said first and second density signals by the other of said first and second density signals to at least substantially eliminate the influence of said at least one further characteristic upon one of said modified signals.

11. The apparatus of claim 9, wherein one of said pointing means includes a source of nuclear radiation.

12. The apparatus of claim 9, wherein one of said pointing means includes a source of X-rays.

13. The apparatus of claim 9, wherein at least one of said pointing means includes a source of optical radiation.

14. The apparatus of claim 9, wherein at least one of said pointing means includes a source of infrared light.

15. The apparatus of claim 9, wherein one of said pointing means includes a source of nuclear radiation and another of said pointing means includes a source of optical radiation, and further comprising means for evaluating said first and second density signals including means for modifying the signal denoting the intensity of optical radiation by the signal denoting the intensity of nuclear radiation.

16. The apparatus of claim 9, wherein one of said pointing means includes a source of nuclear radiation and the other of said pointing means includes a source of optical radiation, and further comprising means for forming the at least one stream with a surplus of fibrous material, means for conveying the stream and its surplus in a predetermined direction along a predetermined path, adjustable trimming means including means for removing the surplus in a predetermined portion of said path, means for evaluating said first and second density signals including means for modifying the signal denoting the intensity of optical radiation by the signal denoting the intensity of nuclear radiation, and means for adjusting said trimming means by the modified signal.

17. The apparatus of claim 16, further comprising means for adjusting said trimming means by the signal denoting the intensity of nuclear radiation so that the adjustment by said modified signal is superimposed upon adjustment by the signal denoting the intensity of nuclear radiation.

18. The apparatus of claim 9, further comprising means for forming the at least one stream with a surplus of fibrous material, means for conveying the stream and its surplus in a predetermined direction along a predetermined path, and trimming means including means for removing the surplus in a predetermined portion of said path, one of said pointing means including a first source of optical radiation which is aimed at the stream upstream of said predetermined portion of the path and the other of said pointing means including a second source of optical radiation which is aimed at the stream downstream of said predetermined portion of the path, and further comprising means for evaluating the signals denoting the intensities of optical radiation from said first and second sources of optical radiation and for generating an additional signal denoting the quantity of surplus which is removed in said predetermined portion of the path.

19. The apparatus of claim 18, wherein said directing means further comprises means for pointing at the stream at least one beam of nuclear radiation and said signal generating means further comprises a device for generating at least one third density signal indicative of the intensity of nuclear radiation which has penetrated through the stream, said evaluating means further comprising means for modifying at least one of the signals denoting intensities of optical radiation by the signal denoting the intensity of nuclear radiation.

20. The apparatus of claim 9, further comprising means for forming at least two discrete streams and means for conveying said streams longitudinally along separate paths, one of said pointing means including a source of nuclear radiation which is aimed at one of the streams and the other of said pointing means including a discrete source of optical radiation for each of said streams and each aimed at the respective stream, one of said devices for generating at least one density signal including means for generating at least one first density signal denoting the intensity of nuclear radiation which has penetrated through the one stream and the other of said devices for generating at least one density signal including means for generating said second density signals each denoting the intensity of optical radiation which has penetrated through the respective stream, and further comprising means for evaluating said first and second density signals including means for modifying the signals denoting the intensities of optical radiation by the signal denoting the intensity of nuclear radiation to at least substantially eliminate the influence of said at least one further characteristic upon the signals denoting the intensities of optical radiation.

21. The apparatus of claim 20, wherein said forming means includes means for forming discrete streams each of which contains a surplus of fibrous material and further comprising adjustable trimming means for each of the streams, each of said trimming means including means for removing the surplus from the respective stream in a predetermined portion of the corresponding path and further comprising means for adjusting each of said trimming means by the respective modified signals.

22. The apparatus of claim 9, further comprising means for forming at least two discrete streams, means for conveying the streams longitudinally in predetermined directions along predetermined paths, means for draping the streams into discrete webs of wrapping material in predetermined portions of the respective paths, and means for subdividing each of the draped streams into a series of rod-shaped articles downstream of the predetermined portions of the respective paths, one of said pointing means including means for aiming at least one beam of nuclear radiation upon successive articles which are obtained as a result of subdivision of at least one of the draped streams and the other of said pointing means including means for aiming at least one discrete beam of optical radiation at each of the streams, one of said devices for generating at least one density signal including means for generating first density signals denoting the intensity of nuclear radiation which has penetrated through the rod-shaped articles and the other of said, devices for generating at least one density signal including means for generating second density signal denoting the intensities of optical radiations which have passed through the stream, and further comprising means for evaluating said first and second density signals by said modifying at least one of said second density signals by said first density signals to at least substantially eliminate the influence of said at least one further characteristic upon one of said modified second density signals.

23. The apparatus of claim 22, wherein said evaluating means further comprises means for modifying the second density signals denoting the density of the stream yielding rod-shaped articles which are traversed by the beam of nuclear radiation.

24. A method of ascertaining the density of at least one stream of fibrous material of the tobacco processing industry, comprising the steps of forming the stream with a surplus of fibrous material; conveying the stream longitudinally in a predetermined direction along a predetermined path; directing at the stream at least one beam of radiation which is capable of penetrating through the stream whereby the intensity of radiation which has penetrated through the stream denotes the density of the stream, said directing step including pointing at least one first beam of optical radiation at the stream in a first portion of said path and pointing at least one second beam of optical radiation at the stream in a second portion of said path; generating at least one density signal which is indicative of said intensity, including generating at least one first density signal indicative of optical radiation which has penetrated across said first portion of said path and at least one second density signal indicative of optical radiation which has penetrated across the second portion of said path; removing the surplus from the stream in a third portion of said path between said first and second portions of said path; and processing said first and second density signals to form an additional signal denoting the quantity of removed surplus.

25. The method of claim 24, wherein said directing step further includes pointing at the stream in said path at least one beam of nuclear radiation which is influenced by at least one further characteristic of the stream in a way other than the said first and second beams of optical radiation, said generating step including generating at least one third density signal indicative of nuclear radiation which has penetrated across said path, and further comprising the step of correcting at least one of said first and second density signals to at least substantially eliminate the influence of said at least one further characteristic upon at least one of said first and second density signals.

26. A method of ascertaining the density of plural streams of fibrous material of the tobacco processing industry, which in addition to density exhibit at least one further variable characteristic including the color and composition of their constituents, comprising the steps of conveying at least one first stream longitudinally along a first predetermined path; forming at least one second stream of fibrous material; conveying the second stream longitudinally along a second predetermined path; directing at said streams beams of radiation which is capable of penetrating through the streams whereby the intensity of radiation which has penetrated through the streams denotes the density of the respective streams, said directing step comprising pointing at the stream in at least one of said paths at least one beam of nuclear radiation which is influenced by the at least one further characteristic in a first manner and pointing against each of said streams at least one beam of optical radiation which is influenced by the at least one further characteristic in a different second manner; generating density signals which are indicative of the density of said streams, including generating a first density signal indicative of the intensity of nuclear radiation which has penetrated through the stream in said at least one path, generating a first second density signal indicative of the intensity of optical radiation which has penetrated through said at least one first stream and generating a second second density signal indicative of the intensity of optical radiation which has penetrated through said at least one second stream; and modifying said first and second second density signals by said first density signal to at least substantially eliminate the influence of said at least one further characteristic upon said first and second second density signals.

27. The method of claim 26, further comprising the step of draping the streams into discrete strips of wrapping material.

28. A method of ascertaining the density of plural streams of fibrous material of the tobacco processing industry, which in addition to density exhibit at least one further variable characteristic including the color and composition of their constituents, comprising the steps of conveying at least one first stream longitudinally along a first predetermined path; forming at least one second stream of fibrous material; conveying the second stream longitudinally along a second predetermined path; draping the streams into discrete strips of wrapping material; subdividing at least one of the draped streams into a succession of discrete rod-shaped articles; directing at said streams beams of radiation which is capable of penetrating through the streams whereby the intensity of radiation which has penetrated through the streams denotes the density of the respective streams, including pointing at the discrete articles at least one beam of nuclear radiation which is influenced by said at least one further characteristic in a first manner and pointing at each of said streams at least one beam of optical radiation which is influenced by said at least one further characteristic in a different second manner; generating density signals which are indicative of the density of said streams, including generating a first density signal indicative of the intensity of nuclear radiation which has penetrated through the discrete articles, generating a first second density signal indicative of the intensity of optical radiation which has penetrated through said at least one first stream and generating a second second density signal indicative of the intensity of optical radiation which has penetrated through said at least one second stream; and modifying at least one of said first and second density second signals by said first density signals to at least substantially eliminate the influence of said at least one further characteristic upon said at least one second density signal.

29. The method of claim 28, further comprising the step of transporting said discrete articles substantially at right angles to their respective longitudinal axes.

30. The method of claim 28, wherein aid modified step includes correcting said second signals denoting the density of the stream, said stream is subdivided into rod-shaped articles.

31. The method of claim 30, wherein subdividing step includes severing said at least one draped stream in a predetermined portion of the respective path so that the severed stream yields a file of successive rod-shaped articles, and further comprising the step of transporting successive rod-shaped articles of the file transversely of their respective longitudinal axes in the form of a row of at least substantially parallel rod-shaped articles.

32. A method of ascertaining the density of at least one stream of fibrous material of the tobacco processing industry, stream, which in addition to density exhibits a variable color, comprising the steps of directing at the stream at least one beam of radiation which is capable of penetrating through the stream whereby the intensity of radiation which has penetrated through the stream denotes the density of the stream, including pointing at the stream at least one beam of a first radiation which is influenced by color changes of the stream in a first manner and pointing at the stream at least one beam of second radiation which is influenced by color changes of the stream in a different second manner; generating at least one density signal which is indicative of said intensity, including generating at least one first density signal indicative of the intensity of first radiation which has penetrated through the stream and generating at least one second density signal indicative of the intensity of second radiation which has penetrated through the stream; and modifying one of said first and second density signals by the other of said first and second density signals to at least substantially eliminate the influence of color changes upon one of said modified signals.

33. A method of ascertaining the density of at least one stream of fibrous material of the tobacco processing industry, which in addition to density exhibits a variable composition including different blends of fibrous material, comprising the steps of directing at the stream at least one beam of radiation which is capable of penetrating through the stream whereby the intensity of radiation which has penetrated through the stream denotes the density of the stream, including pointing at the stream at least one beam of a first radiation which is influenced by composition changes of the stream in a first manner and pointing at the stream at least one beam of a second radiation which is influenced by composition changes of the stream in a different second manner; generating at least one density signal which is indicative of said density, including generating at least one first density signal indicative of the intensity of first radiation which has penetrated through the stream and generating at least one second density signal indicative of the intensity of second radiation which has penetrated through the stream; and modifying one of said first and second density signals to at least substantially eliminate the influence of composition changes upon one of said modified signals.

34. A method of ascertaining the density of at least one stream of fibrous material of the tobacco processing industry, which in addition to density exhibits at least one further variable characteristic including color and composition of its constituents, comprising the steps of continuously building at least one stream in a first portion of a predetermined path so that the stream contains a surplus of fibrous material; conveying the at least one stream longitudinally in a predetermined direction along said path; directing at the at least one stream at least one beam of radiation which is capable of penetrating through the at least one stream whereby the intensity of radiation which has penetrated through the at least one stream denotes the density of the at least one stream, including pointing at the at least one stream at least one beam of nuclear radiation which is influenced by the at least one further characteristic in a first manner and pointing at the at least one stream a beam of optical radiation which is influenced by the at least one further characteristic in a different second manner; generating at least one density signal which is indicative of said intensity, including generating at least one first density signal indicative of the intensity of nuclear radiation which has penetrated through the at least one stream and generating at least one second density signal indicative of the intensity of optical radiation which has penetrated through the at least one stream; removing the surplus in a second portion of said path downstream of said first portion in dependency upon said first density signal; and modifying said second density signal by said first density signal to at least substantially eliminate the influence of the at least one further characteristic from the modified second density signal, said surplus removing step further including regulating the rate of surplus removal in dependency upon the modified second density signal.

35. A method of ascertaining the density of at least one stream of fibrous material of the tobacco processing industry, comprising the steps of forming at least one stream with a surplus of fibrous material; conveying the at least one stream longitudinally in a predetermined direction along a predetermined path; removing the surplus from the at least one stream in a first portion of said path; draping the at least one stream into a strip of wrapping material in a second portion of said path downstream of said first portion; subdividing the draped at least one stream into rod-shaped articles; directing at the at least one stream at least one beam of radiation which is capable of penetrating through the at least one stream whereby the intensity of radiation which has penetrated through the at least one stream denotes the density of the at least one stream, including pointing at successive increments of the at least one stream in said path at least one beam of optical radiation; generating at least one density signal which is indicative of said intensity, including gene rating a series of signals denoting the densities of successive increments of the at least one stream; comparing the signals of said series with a reference signal denoting a predetermined range of acceptable densities; and utilizing the signals which are outside of said range to segregate the respective rod-shaped articles from the remaining rod-shaped articles.

36. Apparatus for processing at least one stream of the tobacco processing industry, comprising means for conveying the at least one stream along a predetermined path; and density monitoring means including means for directing at the at least one stream at least one beam of radiation which is capable of penetrating through the at least one stream whereby the intensity of radiation which has penetrated through the at least one stream denotes the density of the at least one stream, and means for generating at least one density signal which is indicative of said intensity, said directing means including at least one source of optical radiation which is aimed at the at least one stream at one side of said path so that the radiation penetrates through the at least one stream and through the conveying means, said signal generating means including a device for generating at least one density signal indicative of optical radiation which has penetrated through the at least one stream and through said conveying means, said device being disposed at the other side of said path.

37. Apparatus for processing at least one stream of fibrous material of the tobacco processing industry, comprising density monitoring means including means for directing at the at least one stream at least one beam of radiation which is capable of penetrating through the at least one stream whereby the intensity of radiation which has penetrated through the at least one stream denotes the density of the at least one stream, and means for generating at least one density signal which is indicative of said intensity, said signal generating means including an optoelectronic transducer and said directing means including several sources of radiation each arranged to point a beam of radiation at the at least one stream so that the radiation which has penetrated through the at least one stream impinges upon said transducer.

38. Apparatus for processing at least one stream of fibrous material of the tobacco processing industry, comprising means for forming the at least one stream with a surplus of fibrous material; means for conveying the at least one stream and its surplus in a predetermined direction along a predetermined path; adjustable means for removing the surplus in a predetermined portion of said path; means for subdividing the stream into rod-shaped articles downstream of the predetermined portion of said path; density monitoring means including means for directing at the at least one stream at least one beam of radiation which is capable of penetrating through the at least one stream whereby the intensity of radiation which has penetrated through the at least one stream denotes the density of the at least one stream, and means for generating at least one density signal which is indicative of said intensity, said directing means including means for pointing at least one beam of optical radiation at the at least one stream in said path and means for pointing at the at least one stream at least one beam of nuclear radiation, said signal generating means including a device for generating first signals denoting the intensity of optical radiation which has penetrated through successive increments of the conveyed at least one stream so that the generated first signals denote the density of successive increments of the at least one stream, said signal generating means further comprising a device for generating second signals denoting the intensity of nuclear radiation which has penetrated through the as least one stream; means for evaluating said first signals including a source of reference signals denoting the range of acceptable densities and means for comparing said first articles containing stream increments whose densities are outside of said range from the remaining articles; and means for adjusting said surplus removing means by said second signals.

* * * * *

UNITED STATES PATENT AND TRADEMARK OFFICE
CERTIFICATE OF CORRECTION

PATENT NO. : 4,865,054

DATED : September 12, 1989

INVENTOR(S) : Heinz-Christen LORENZEN et al.

It is certified that error appears in the above-identified patent and that said Letters Patent are hereby corrected as shown below:

Col. 30, line 41, "stream," should be deleted.
Col. 34, line 4, after "first" insert --signals with said reference signals; means for segregating the--.

Signed and Sealed this

Tenth Day of March, 1992

Attest:

Attesting Officer

HARRY F. MANBECK, JR.

Commissioner of Patents and Trademarks